(12) United States Patent
Moorman et al.

(10) Patent No.: US 7,342,003 B2
(45) Date of Patent: **\*Mar. 11, 2008**

(54) SYNTHESIS OF 2-ARALKYLOXYADENOSINES, 2-ALKOXYADENOSINES, AND THEIR ANALOGS

(75) Inventors: Allan R. Moorman, Durham, NC (US); Michael Scannell, Holly Springs, NC (US); Thiagarajan Balasubramanian, Cary, NC (US); Russell Outcalt, Cary, NC (US); Edward Leung, Cary, NC (US)

(73) Assignee: King Pharmaceuticals Research and Development, Inc., Cary, NC (US)

( * ) Notice: Subject to any disclaimer, the term of this patent is extended or adjusted under 35 U.S.C. 154(b) by 25 days.

This patent is subject to a terminal disclaimer.

(21) Appl. No.: 11/155,212

(22) Filed: Jun. 16, 2005

(65) Prior Publication Data

US 2006/0135466 A1    Jun. 22, 2006

Related U.S. Application Data

(63) Continuation of application No. 10/958,470, filed on Oct. 4, 2004, now abandoned, and a continuation-in-part of application No. 10/281,291, filed on Oct. 24, 2002, now Pat. No. 6,951,932.

(60) Provisional application No. 60/508,804, filed on Oct. 3, 2003, provisional application No. 60/375,723, filed on Apr. 26, 2002, provisional application No. 60/335,169, filed on Oct. 25, 2001.

(51) Int. Cl.
  *C07H 19/167* (2006.01)
  *A61K 31/70* (2006.01)

(52) U.S. Cl. .................. 514/46; 536/27.62; 536/27.63; 536/27.7; 536/27.11

(58) Field of Classification Search ............. 536/27.11, 536/27.62, 27.63, 27.7; 514/46
See application file for complete search history.

(56) References Cited

U.S. PATENT DOCUMENTS

| | | | |
|---|---|---|---|
| 5,140,015 A | 8/1992 | Olsson et al. | 514/46 |
| 5,430,027 A | 7/1995 | Knutsen et al. | 514/46 |
| 5,432,164 A | 7/1995 | Knutsen et al. | 514/46 |
| 5,484,774 A | 1/1996 | Lau et al. | 514/46 |
| 5,578,582 A | 11/1996 | Knutsen et al. | 514/46 |
| 5,654,285 A | 8/1997 | Ingall et al. | 514/47 |
| 5,683,989 A | 11/1997 | Lau et al. | 514/46 |
| 6,951,932 B2 | 10/2005 | Moorman | 536/27.6 |

FOREIGN PATENT DOCUMENTS

| | | |
|---|---|---|
| DE | 2258378 | 6/1973 |
| DE | 2324130 | 11/1973 |
| JP | 49-20198 | 2/1974 |
| JP | 49-124096 | 11/1974 |
| JP | 50-53393 | 5/1975 |
| WO | WO97/33591 | 9/1997 |

OTHER PUBLICATIONS

[R] Victor-Vega et al., "Adenosine 14 A2A Receptor Agonists Promote More Rapid Wound Healing than Recombinant Human Platelet-Derived Growth Factor (Becaplermin Gel)," Inflammation, 26(1), 19-24 (Feb. 2002).*
R. Olsson et al., "Synthesis and Cardiac Pharmacology of 2-(AR)Alkoxyadenosines," Nucleosides & Nucleotides, vol. 10, No. 5, 1991, pp. 1049-1055.
H. Schaeffer et al., "Synthesis of Potential Anticancer Agents. XIV. Ribosides of 2,6-Disubstituted Purines," J. Am. Chem. Soc. vol. 80, 1958, pp. 3738-3742. Jul. 20, 1958.
M. Ueeda et al., "2-Alkoxyadenosines: Potent and Selective Agonists at the Coronary Artery $A_2$ Adenosine Receptor," J. Med. Chem., 1991, vol. 34, No. 4, pp. 1334-1339.
M. Ueeda et al., "2-Aralkoxyadenosines: Potent and Selective Agonists at the Coronary Artery $A_2$ Adenosine Receptor," J. Med. Chem. , 1991, vol. 34, No. 4, pp. 1340-1344.
R. Barlett et al., "Synthesis and Pharmacological Evaluation of a Series of Analogues of 1-Methylisoguanosine," J. Med. Chem., 1981, vol. 24, No. 8, pp. 947-954.
K. Miyai et al.; "Synthesis and Anti-Deoxyribonucleic Avcid Virus Activity of certain 9-β-D-Arabinofuranosyl-2-substituted Adenosine Derivatives," J. Med. Chem., 1974, vol. 17, No. 2, pp. 242-244.
Halbfinger et al., "Molecular Recognition of Modified Adenine Nucleotides by the P2yl -Receptor. 1.A Synthetic, Biochemical, and NMR Approach," J. of Med. Chem. , 1999, vol. 42, No. 26, pp. 5325-5337 (WEB Dec. 4, 1999).
Wanner et al., "2-Nitro Analogues of Adenosine and l-Deazaadenosine: Synthesis and Binding Studies at the Adenosine A1, A2A, A3 Receptor Subtypes," Bioorganic & Medicinal Chemistry Letters, Sep. 18, 2000, vol. 10, No. 18, pp. 2141-2144.
Robins et al., "Nucleic Acid Related Compounds. 114. Synthesis of 2,6-(Disubstituted)purine 2',3'-Dinucleosides and Selected Cytotoxic, Anti-Hepatitis B, and Adenosine Deaminase Substrate Activities", J. of Heterocyclic Chemistry, Nov.-Dec. 2001, vol. 38, No. 6, pp. 1297-1306.
Marumoto et al., "Synthesis and Enzymatic Activity of Adenosine 3', 5'-Cyclic Phosphate Analogs," Chem. & Pharm. Bulletin, Apr. 1979, vol. 27, No. 4, pp. 990-1003.
Marumoto et al., "Synthesis and Coronary Vasodilating Activity of 2-Substituted Adenosines," Chem & Pharm. Bulletin (Japan), 1975, vol. 23, No. 4, pp. 759-774.

(Continued)

*Primary Examiner*—L. E. Crane
(74) *Attorney, Agent, or Firm*—Paivi Kukkola

(57) ABSTRACT

Provided is a method for the synthesis of an aralkyloxyadenosine or an alkoxyadenosine. The method includes protecting the hydroxyl sugar groups with a protecting group to produce a protected halogenated adenosine. The protected halogenated adenosine is alkoxylated, and the hydroxyl sugar groups of the protected halogenated adenosine are deprotected to provide the aralkyloxyadenosine or alkoxyadenosine.

25 Claims, 1 Drawing Sheet

OTHER PUBLICATIONS

Smith et al., "March's Advanced Organic Chemistry—Reactions, Mechanisms, and Structure," New York, NY John Wiley & Sons, Inc. 2001, Fifth Edition, pp. 486-487.

Kochetkov et al., "Organic Chemistry of Nucleic Acids, Part B," New York Plenum Press, 1972, p. 453.

Copy of Search Report for PCT/US04/32762, May 19, 2005.

Victor-Vega et al, "Adenosine $A_{2A}$ Receptor Agonists Promote more Rapid Wound Healing than Recombinant Human Platelet-Derived growth Factor (Becaplermin Gel)", *Inflammation*, vol. 26, No. 1, 2002, 19-24.

* cited by examiner

SYNTHESIS OF 2-ARALKYLOXYADENOSINES, 2-ALKOXYADENOSINES, AND THEIR ANALOGS

This application is a continuation of U.S. application Ser. No. 10/958,470, filed Oct. 4, 2004, now abandoned, which claims the benefit of U.S. Provisional Application No. 60/508,804, filed Oct. 3, 2003; and a continuation-in-part of U.S. application Ser No. 10/281,291, filed Oct. 24, 2002, now U.S. Pat. No. 6,951,932, which claims the benefit of U.S. Provisional Application No. 60/335,169, filed Oct. 25, 2001 and U.S. Provisional Application No. 60/375,723, filed Apr. 26, 2002.

BACKGROUND

1. Field of the Invention

This invention provides a method for the synthesis of 2-aralkyloxyadenosines and 2-alkoxyadenosines. The invention is particularly useful for the synthesis of 2-[2-(4-chlorophenyl)ethoxy]adenosine.

2. Description of the Related Art

It is generally thought that adenosine has a number of biological functions through its activation of four cell membrane receptors classified as $A_1$, $A_{2A}$, $A_{2B}$, and $A_3$. These receptors are believed to elicit their biological activities through typical signal transduction pathways.

Chemical analogs of adenosine can function as either agonists or antagonists and may bind selectively to the individual subclasses of adenosine receptors. For example, it has been demonstrated that selective adenosine $A_{2A}$ receptor agonists, when applied topically, can significantly accelerate wound healing with both normal and impaired healing capacity. In particular, it has been shown that 2-[2-(4-chlorophenyl)ethoxy]adenosine promotes more rapid closure of excisional wounds in normal healthy mice than 0.01% becaplermin gel, an agent currently approved for use in the treatment of diabetic foot ulcers.

The preparation of 2-[2-(4-chlorophenyl)ethoxy]-adenosine and other 2-aralkoxyadenosines and 2-alkoxyadenosines has typically heretofore involved the displacement of the chloro group of 2',3'-O-(ethoxymethylidene)-2-chloroadenosine or 2',3'-O-(isopropylidene)-2-chloroadenosine with the appropriate sodium or lithium (Ar)alkoxide followed by de-protection and purification of the desired product. Blocking of the 2'- and 3'-hydroxyl groups is generally considered to be important to prevent the formation of a 2-2' polymeric product. It has also been indicated that the lability of the glycosidic N-9 C-1' bond to the acidic conditions required to remove the 2',3'-blocking group contributes to the low yields observed in the preparation of these selective adenosine $A_{2A}$ agonists.

However, these synthetic routes are lengthy and often produce compounds in low yield, and that are difficult to purify. It would be desirable to have new methods to synthesize 2-aralkyloxyadenosines and 2-alkoxyadenosines. Preferably new synthetic processes would be scalable, would produce the desired compound with a high purity, and not least important, would reduce the cost of producing the desired compound on a large scale. It would be particularly desirable to develop new methods to synthesize 2-[2-(4-chlorophenyl)ethoxy]adenosine.

BRIEF SUMMARY OF THE INVENTION

A practical process that solves many of the problems of prior art methods for the synthesis of 2-[2-(4-chlorophenyl) ethoxy]adenosine and its analogs is herein presented. This method provides advantages in cost, efficiency, and purity of the final product. This route provides several advantages, the reaction is not highly variable and dependent on the lot of alkoxide used, whether conducted neat or in various solvents. This invention also provides advantages in scalability and cost all while producing a high purity final product. The general scheme of this invention is shown in FIG. 1.

This invention involves protecting the sugar hydroxyl groups with a protecting group, followed by alkoxylation, and then de-protection and recovery of the final product, a 2-alkoxyadenosine or 2-arylalkoxyadenosine. In certain preferred embodiments the protecting group is a tri-alkylsilyl group and deprotection is effected with fluoride anion. In certain other preferred embodiments, the protecting group is tert-butyl dimethylsilyl and the de-protection is accomplished with an ammonium fluoride salt.

DETAILED DESCRIPTION OF THE INVENTION

Figure 1:
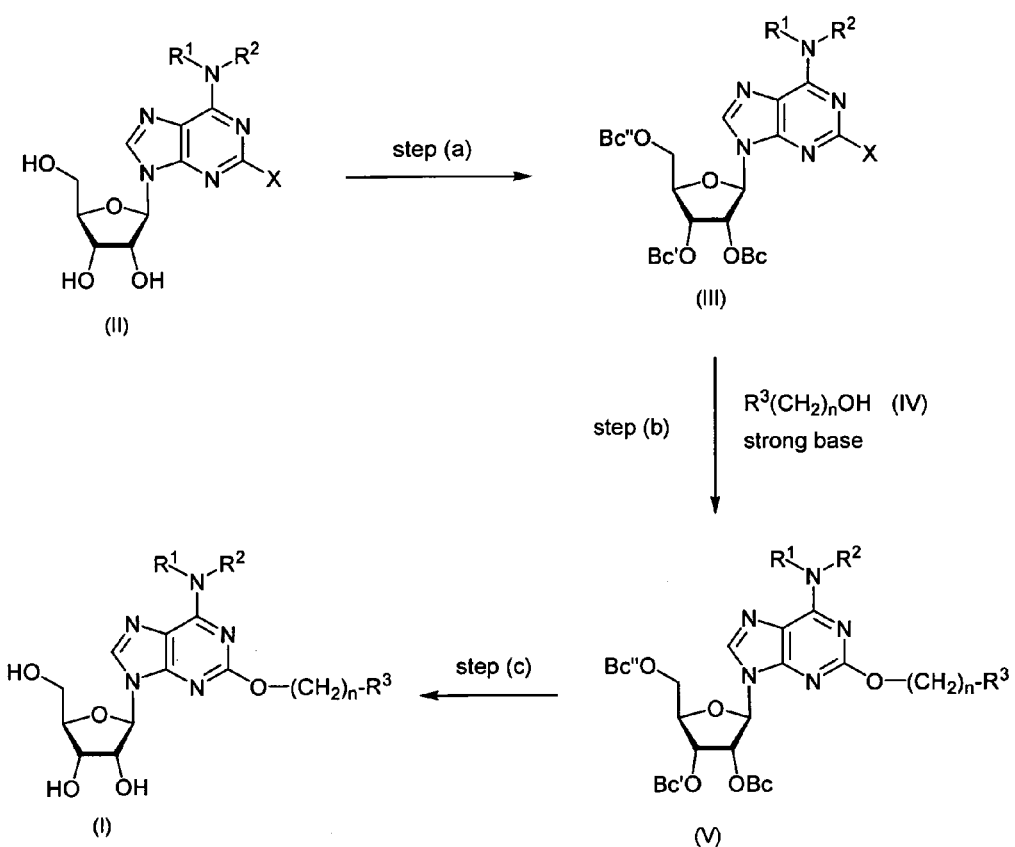
FIG. 1 shows the general scheme for the preparation of the compounds of this invention.

FIG. 1 shows the general process of this invention. Here X is halo or halide; $R^1$ and $R^2$ are independently hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aralkyl, substituted aralkyl, aryl, substituted aryl, heteroaryl, heterocyclic, or if taken together with the nitrogen atom, form an azetidine ring or a 5–6 membered heterocyclic ring containing a total of one to four heteroatoms selected from nitrogen, oxygen, and sulfur.

In certain preferred methods of the invention the halogenated adenosine starting material is selected from compounds of the formula:

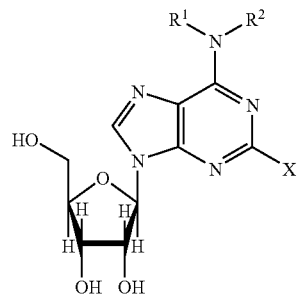

wherein $R^1$ and $R^2$ are independently selected from hydrogen, $C_1$–$C_6$ alkyl, $C_2$–$C_6$ alkenyl, $C_2$–$C_6$ alkynyl, $C_3$–$C_8$ cycloalkyl, $C_3$–$C_8$ cycloalkenyl, $C_7$–$C_{12}$ aralkyl, $C_8$–$C_{12}$ aryl, 5–7 membered heteroaryl, and 4–7 membered heterocycloalkyl, each of which is optionally substituted with 1 to 3 substituents independently selected from the group consisting of $C_1$–$C_6$ alkyl, $C_1$–$C_6$ alkoxy, amino, mono-($C_1$–$C_6$ alkyl)amino, di-($C_1$–$C_6$ alkyl)amino, halogen, hydroxy, cyano, nitro, carboxylate, carboxamide, sulfonate, and sulfonamide; or $NR^1R^1R^2$ taken in combination forms a 4–7 membered heterocyoloalkyl or a 5–7 membered heteroaryl group, each of which is optionally substituted with 1 to 3 substituents independently selected from the group consisting of $C_1$–$C_6$ alkyl, $C_{1-C6}$ alkoxy, amino, mono-($C_1$–$C_6$ alkyl)amino, di- ($C_1$–$C_6$ alkyl)amino, halogen, hydroxy, cyana, nitro, carboxylate, carboxamide, sulfonate, and sulfonamide; and X is halogen, mesylate, tosylate, or triflate.

In certain preferred methods, $R^1$ and $R^2$ are hydrogen.

Alkylsulfonates and arylsulfonates are often referred to as pseudohalides due to their reactivity profile which substantially mimics halogen atoms. Thus, the invention contemplates the use of halogenated adenosine compounds in which X is fluoro, chloro, bromo and iodo and also those compounds in which X is a pseudo-halide, $RSO_2$—, such as mesylate, tosylate, or triflate.

The aralkoxy or alkoxy adenosines of this invention are prepared by a route in which the sugar hydroxyl groups are first protected with a the same or different protecting groups (referred to in FIG. 1 as Bc, Bc' and Bc" for blocking group) as shown in FIG. 1, step (a), then the alkoxylation step is performed as illustrated in step (b), and then the sugar hydroxyl groups are de-protected after alkoxylation to produce the final product as shown in step (c).

The use of the blocking groups of this invention provides the advantage of greatly improving the reliability and ease with which the alkoxylation can be performed. Most importantly, by this route the reaction is not highly variable and dependent on the lot of alkoxide used, whether conducted neat or in various solvents. This invention also is scalable and can produce muti-kilogram batches, and further avoids the necessity of high pressure reactions. This route also reduces the cost of starting materials and the overall cost of goods. The invention concomitantly provides a final product with a high purity profile.

In FIG. 1, step (a), a 2-haloadenosine of formula (II) is protected with the same or different blocking groups to produce intermediate of formula (III). Certain preferred blocking groups include acetyl, benzyl, benzoyl, 4-methoxybenzyl, trialkylsilyl, and tetraalkyl-disiloxandiyl groups. Certain more preferred blocking groups include tertbutyl dimethylsilyl, triethylsilyl, isopropyl-diethylsilyl, triisopropylsilyl, isopropyl-dimethylsilyl, or diisopropylethylsilyl. In step (b), the protected 2-chloroadenosine of formula (III) is then (ar)alkoxylated to form the (ar)alkoxy intermediate of formula (V). This (ar)alkoxylation is performed with the addition of a strong base such as a metal hydride (preferably sodium hydride, lithium hydride, potassium hydride, or calcium hydride) to the alcohol of formula (IV) neat. Generally, the addition of solvents at this stage prevents (ar)alkoxide formation or results in degradation. Preferably the reaction is conducted with at least 2.5 ml of alcohol per gram of protected 2-chloroadenosine.

On a larger scale the alcohol medium causes the production of a certain amount of mixed fractions when using silica filtration. To minimize this, the reaction mixture was concentrated to approximately 20% of its original volume via vacuum distillation. This caused an increase in the amount of partially protected material. However these polar intermediates were easily eluted from the plug with methanol/dichloromethane.

The alkoxy or aralkoxy intermediate is then de-protected in step (c), producing the final product. De-protection is preferably accomplished with ammonium fluoride due to its efficiency and ease of removal in workup. Tetrabutyl ammonium fluoride, hydrogen fluoride-pyridine, and triethylamine trihydrofluoride can also be used.

The methods of this invention also provide advantages in cost when compared with prior art methods.

In certain aspects, the invention provides that protecting groups which are suitable for blocking or masking the sugar hydroxyl residues include various silyl groups, alkanoyl, aryl, aroyl, and aralkyl groups.

Certain preferred silyl groups, which are suitable for use as hydroxyl blocking groups, include one or more silyl groups, a 1,3-disiloxan-diyl group, or a combination thereof. For example, the silyl protecting group may include silyl groups of the formula, —$SiR_AR_BR_C$, wherein $R_A$, $R_B$, and $R_C$ are independently selected from $C_{1-C6}$ alkyl, phenyl, and benzyl.

Certain preferred silyl protecting groups include, but are not limited to silyl groups of the formula, —$SiR_AR_BR_C$, wherein $R_A$, $R_B$, and $R_C$ are independently selected from $C_{1-c6}$ alkyl, phenyl, and benzyl, or more preferably those groups in which $R_A$ is $C_3$–$C_6$ alkyl and $R_B$ and $R_C$ are independently selected from $C_1$–$C_4$ alkyl. Typically preferred silyl protecting groups include tert-butyl dimethylsilyl, triethylsilyl, isopropyl-diethylsilyl, triisopropylsilyl, isopropyl-dimethylsilyl, or diisopropylethylsilyl.

In certain embodiments it may be desirable to replace to mono-coordinated silyl masking or blocking groups with a chelating disiloxan-diyl blocking group which is capable of masking two hydroxyl residues. Certain preferred examples of disiloxan-diyl blocking groups include 1,1,3,3-tetraethyl-disiloxan-1,3-diyl and 1,1,3,3-tetraisopropyl-disiloxan-1,3-diyl, each of which may be used in combination with one or more trialkylsilyl blocking groups such as —$SiR_AR_BR_C$ groups wherein $R_A$, $R_B$, and $R_C$ are independently selected from $C_1$–$C_6$ alkyl.

In certain other aspects, it may be desirable to incorporate one or more non-silyl blocking groups. Thus, the invention contemplates synthetic methods in which the protecting group is selected from $C_2$–$C_6$ alkanoyl groups or aralkyl groups. A preferred alkanoyl groups is acetyl. Certain preferred aralkyl or aroyl protecting groups include benzyl or benzoyl each of which is substituted with between 0–3 substituents independently selected from the group consisting of methyl, ethyl, methoxy, ethoxy, fluoro, chloro, and bromo. Typically preferred aralkyl protecting groups include benzyl or 4-methoxybenzyl.

In certain aspects, the invention provides for the de-protection of the masked or blocked hydroxyl sugar groups by treatment of the protected adenosine with a fluoride salt. For methods in which a silyl blocking or masking group is used, fluoride salts are generally used as a fast, mild deprotection agent. Thus, in certain preferred methods the fluoride salt comprises a non-coordinating or weakly coordinating cation, or more preferably, the fluoride salt comprises a tetra($C_1$–$C_{10}$)alkylammonium cation. Certain preferred fluoride salts which are suitable for use in deprotection of silyl protected hydroxyl sugar groups include tetramethylammonium fluoride, tetraethylammonium fluoride, or tetrabutylammonium fluoride.

Certain other deprotecting agents suitable for use in the methods of the invention include base adducts of hydrogen fluoride. Certain preferred hydrogen fluoride base adducts include hydrogen fluoride-pyridine, hydrogen fluoride-pyrazine, hydrogen fluoride-pyrimidine, hydrogen fluoride-trialkylamine, hydrogen fluoride-piperidine, hydrogen fluoride-pyrrole, hydrogen fluoride-pyrrolidine. Certain particularly preferred hydrogen fluoride base adducts include triethylamine trihydrofluoride or hydrogen fluoride-pyridine.

As used herein, the term halo or halogen refers to fluoro, chloro, bromo, and iodo. The term alkyl refers to monovalent straight, branched, or cyclic alkyl groups preferably having from 1 to 20 carbon atoms, most preferably 1 to 10 carbon atoms (lower alkyl). This term is exemplified by groups such as methyl, ethyl, n-propyl, iso-propyl, n-butyl, iso-butyl, n-hexyl, 2-methylpropyl, 3-methylbutyl, and the like. The terms alkylene and lower alkylene refer to divalent radicals of the corresponding alkane. Further, as used herein, other moieties having names derived from alkanes, such as alkoxy, alkanoyl, alkenyl, cycloalkenyl, etc., when modified by lower, have carbon chains of ten or fewer carbon atoms. In those cases where the minimum number of carbons required are greater than one, e.g., alkenyl and alkynyl (minimum of two carbons) and cycloalkyl (minimum of three carbon atoms), it is to be understood that the term lower means at least the minimum number of carbon atoms.

As used herein, the term substituted alkyl refers to an alkyl group, having from 1 to 5 substituents, and preferably from 1 to 3 substituents, selected from the group consisting of alkoxy, substituted alkoxy, cycloalkoxy, substituted cycloalkoxy, cycloalkyl, substituted cycloalkyl, cycloalkenyl, substituted cycloalkenyl, alkynyl, substituted alkynyl, acyl, amino, aryl, substituted aryl, carboxyl, carboxyalkyl, cyano, fluoro, hydroxyl, halogen, heteroaryl, heterocyclic, nitro, alkylthio, thiol, mono(alkyl)-amino, di(alkyl)amino, mono(substituted alkyl)amino, di(substituted alkyl)amino, unsymmetric disubstituted amines having different substituents selected from alkyl, substituted alkyl, aryl, substituted aryl, aralkyl, and substituted aralkyl, —SO-alkyl, —SO-substituted alkyl, —SO-aryl, —SO-substituted aryl, —$SO_2$-alkyl, —$SO_2$-substituted alkyl, —$SO_2$-aryl, and —$SO_2$-substituted aryl. As used herein, other moieties having the prefix substituted are intended to include one or more of the substituents listed above.

As used herein, the term alkenyl refers to straight or branched alkenyl groups having from 2 to 20, most preferably from 2 to 10 carbon atoms and having at least 1 and preferably from 1 to 3 sites of alkenyl unsaturation. This term is exemplified by groups such as ethenyl ($CH=CH_2$), 1-propenyl ($CH=CH-CH_3$), 2-propenyl ($C(CH_3)=CH_2$), 3-methyl-2-pentenyl ($CH_2-CH=C(CH_3)-CH_2CH_3$), an the like.

As used herein, the term alkynyl refers to straight or branched alkynyl groups having from 2 to 20 carbon atoms, most preferably from 2 to 10 carbon atoms and having at least 1 and preferably from 1 to 2 sites of alkynyl unsaturation. This term is exemplified by groups such as ethynyl, 1-propynyl, 2-propynyl, 2-butynyl, 4,4-dimethyl-2-pentynyl, and the like.

As used herein, the term cycloalkyl refers to cyclic alkyl groups of from 3 to 20 carbon atoms having a single cyclic ring or multiple rings joined in either a fused or spirocyclic condensation. This term is exemplified by groups such as cyclopropyl, cyclopentyl, cyclohexyl, cyclooctyl, norbornyl, perhydrofluorenyl, adamantyl, and the like.

As used herein, the term cycloalkenyl refers to cyclic alkenyl groups of from 5 to 20 carbon atoms having a single cyclic ring or multiple rings joined in either a fused or spirocyclic condensation and having at least 1 and preferably from 1 to 2 sites of alkenyl unsaturation. This term is exemplified by groups such as cyclopentenyl, cycloheptenyl, 1,3-cyclooctadienyl, cycloheptatrienyl, bicyclo[2.2.1]hepta-2,5-dienyl, and the like.

As used herein, the term aryl refers to an unsaturated, aromatic, carbocyclic group of from 6 to 20 carbon atoms having a single ring or multiple condensed rings. This term is exemplified by groups such as phenyl, 1-naphthyl, 2-naphthyl, anthracenyl, 1,2-benzanthracenyl, and the like. As used herein, the term aryl also refers to those fused-ring hydrocarbons in which the aromatic ring or rings are condensed to additional non-aromatic rings. In this manner, this term is exemplified by groups such as fluorenyl, acenaphthenyl, biphenylenyl, fluoranthenyl, and the like. Unless otherwise constrained by the definition for the aryl substituent, such aryl groups can optionally be substituted with from one to five substituents, preferably one to three substituents, selected from the list given herein.

As used herein, the term aralkyl refers to an aryl or substituted aryl group, attached to an alkylene group or substituted alkylene group, where aryl, substituted aryl, alkylene, and substituted alkylene are as defined herein.

As used herein, the term heterocyclic refers to a monovalent saturated or unsaturated carbocyclic group having a single ring or multiple condensed rings, from 1 to 15 carbon atoms and from 1 to 5 heteroatoms within the ring or rings, preferably from 1 to 9 carbon atoms and from 1 to 4 heteroatoms within the ring or rings, selected from the group of heteroatoms consisting of nitrogen, sulfur, and oxygen. This term is exemplified by groups such as tetrahydrofuranyl, pyrrolinyl, pyrrolidinyl, oxazolidinyl, thiazolidinyl, imidazolinyl, imidazolidinyl, piperidinyl, piperazinyl, quinuclidinyl, thiomorpholinyl, morpholinyl, dioxolanyl, and the like.

As used herein, the term heteroaryl refers to a 5-membered or 6-membered heterocyclic, aromatic group, which can optionally be fused to an aryl or substituted aryl ring, where heterocyclic, aryl, and substituted aryl are as defined herein. This term is exemplified by groups such as pyrrolyl, furanyl, thiophenyl, pyrazolyl, imidazolyl, isoxazolyl, oxazolyl, isothiazolyl, thiazolyl, thiadiazolyl, triazolyl, tetrazolyl, pyridyl, pyridazyl, pyrimidyl, indolyl, benzofuranyl, benzotriazolyl, quinolinyl, isoquinolinyl, and the like. Optionally, the heteroaryl group may be fused to a second or third heteroaryl group. In this context, this term is exemplified by groups such as 1,2,3-triazolo[4,5-b]pyridinyl, s-triazolo[1,5-a]pyrimidinyl, pyrazolo[3,4-d]pyrimidinyl, purinyl, pterinyl, pteridinyl, pyrimido[5,4-d]pyrimidinyl, and the like.

As used herein, the term alkoxy refers to the group alkyl-O—, substituted alkyl-O—, cycloalkyl-O—, or substituted cycloalkyl-O— where alkyl, substituted alkyl, cycloalkyl, and substituted cycloalkyl are as defined herein. This term is exemplified by such groups as methoxy, ethoxy, 1-propoxy, 2-propoxy, 1-butyloxy, tert-butyloxy, cyclopentyloxy, cyclohexylethoxy, and the like.

As used herein, the term arylalkoxy means an aryl substituted alkoxy group with the terms aryl and alkoxy as defined above.

EXAMPLES

General procedure. The first step in the process involves the protection of 2-chloroadenosine of formula (II) to yield the intermediate of formula (III). This material, consisting mainly of the product and some polar contaminants (presumably silanols when a silane protecting group is employed, an alcohol when an aralkyl protecting group is employed or a carboxylic acid when an alkanoyl or aroyl protecting group is employed), is used without further purification in the next step. The compound of formula (III), e.g., trisilylated material, is then alkoxylated using, e.g., NaH, in neat alcohol of formula (IV) to afford intermediate of formula (V). The crude reaction mixture is distilled under vacuum at 130° C. to remove approximately 70% of the alcohol used. The resultant oil which is a mixture of fully and partially protected intermediates (approximately 2.5:1:1 tri:bis:mono) is passed through a silica plug to remove residual alcohol. These intermediates are deprotected with, e.g., ammonium fluoride, and the product is recrystallized from ethanol to yield, e.g., the compound of Examnle 3 as a white solid with an overall yield of 40.7%, and a purity of 98.9%.

A significant amount of mixed fractions are isolated from the plug that contains both the alcohol and intermediate 3. In order to recover more material, the mixed fractions are de-protected with ammonium fluoride and the resultant solids are triturated with heptane to remove the alcohol. Recrystallization twice from ethanol yields additional product. The first recrystallization from ethanol requires less ethanol (1 ml/g of crude product) than the second (5 ml/g of crude product) due to the significant amount of 2-(4-chlorophenyl)-ethanol still present.

Example 1

Preparation of 2-Chloro-2', 3', 5'-tri-O-(tert-butyldimethylsilyl)adenosine

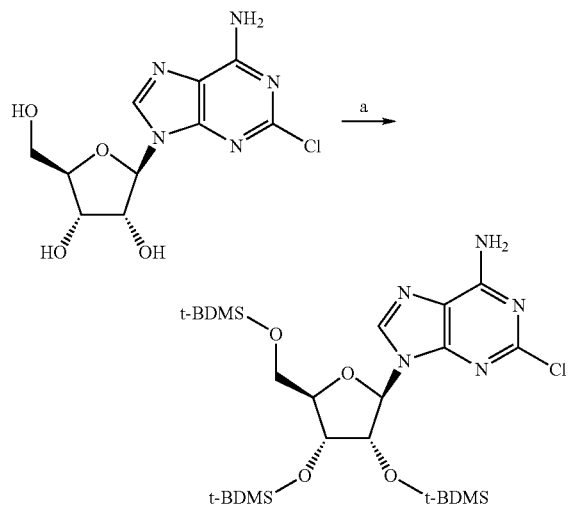

To a stirred solution of 2001 g (6.632 mol) of 2-chloroadenosine and 9,997 g (66.32 mol) of t-butyldimethylsilyl chloride in 26 L of anhydrous tetrahydrofuran and 16 L of DMF was added 9030 g (132.6 mol) of imidazole. Upon disappearance of the starting material (2-chloroadenosine) by TLC, the reaction was concentrated under reduced pressure. The resultant viscous oil was diluted with ethyl acetate (20 L) and washed with 2M NaOH (20 L), and three times with water (20 L each time). The organic layer was dried over magnesium sulfate (1000 g), filtered and the solvent removed under reduced pressure. The residual oil was used in the next step without further purification.

Example 2

Preparation of 6-amino-2-[2-(4-chlorophenyl) ethoxy]-9-(2,3,5-tri-O-tert-butyl dimethylsilyl-β-D-ribofuranosyl)purine

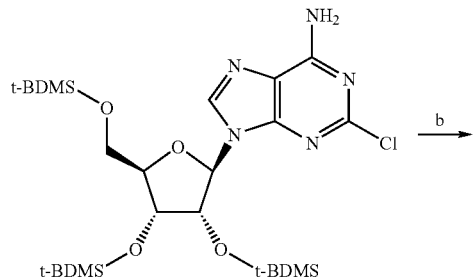

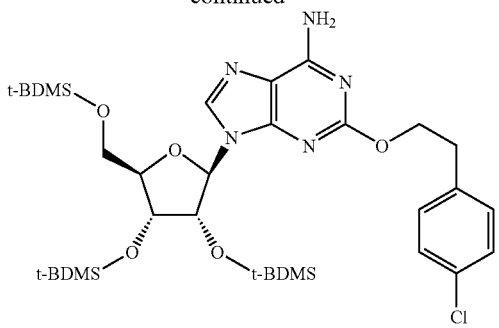

To a solution of 2-chloro-2',3',5'-tri-O-(tert-butyldimethylsilyl)-adenosine (5526 g) in 2-(4-chlorophenyl)-ethanol (17.4 L) was added 1.326 g (33.16 mol) of sodium hydride, portion-wise to control gas evolution. Upon the disappearance of the starting material (2-chloro-2',3',5'-tri-O-(tert-butyldimethylsilyl)adenosine by HPLC, the reaction was diluted with water (55.3 L). The product was extracted into ethyl acetate (57 L) and washed with brine (55.2 L). The organic layer was dried over magnesium sulfate, filtered and concentrated under reduced pressure to yield 26.130 g of a viscous oil. The reaction mixture was concentrated under vacuum at 130° C. to remove 17.770 g of 2-(4-chlorophenyl)-ethanol. The remaining material was passed through a silica plug eluting with dichloromethane to remove residual alcohol and 95:5 dichloromethane:methanol to elute the product as a foamy solid (3448.4 g, 67.9% yield). The mixed fractions were concentrated and processed separately to produce a second batch of product.

Example 3

Preparation of 2-[2-(4-chlorophenyl)ethoxy]-adenosine

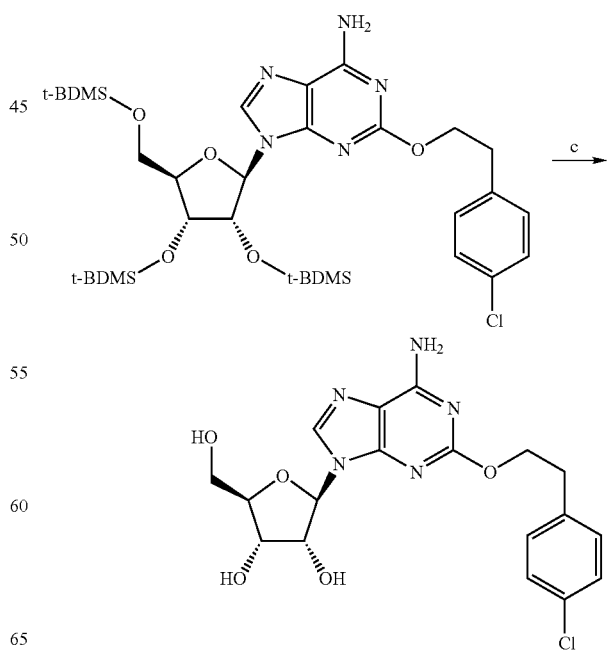

To a solution of 3438.4 g (4.51 mol) of 6-amino-2-[2-(4-chlorophenyl)ethoxy]-9-(2,3,5-tri-O-tert-butyldimethyl-β-D-ribofuranosyl)purine in 48.4 L of methanol was added 1.679 g (45.32 mol) of ammonium fluoride. The solution was heated to reflux and monitored by HPLC to determine completion. The reaction was allowed to cool to room temperature and the solvent was concentrated under reduced pressure. The reaction mixture was partitioned between water (17.3 L) and ethyl acetate (17.3 L). The aqueous layer was washed again with ethyl acetate (17.4 L). The combined organic layers were dried over magnesium sulfate (1000 g), filtered and removed under reduced pressure. The resultant solid was recrystallized from ethanol (9.87 L) to yield an off-white solid (1139 g, 59.8% yield).

Example 4

2-Chloro-2',3',5'-tri-O-(triethylsilyl)adenosine

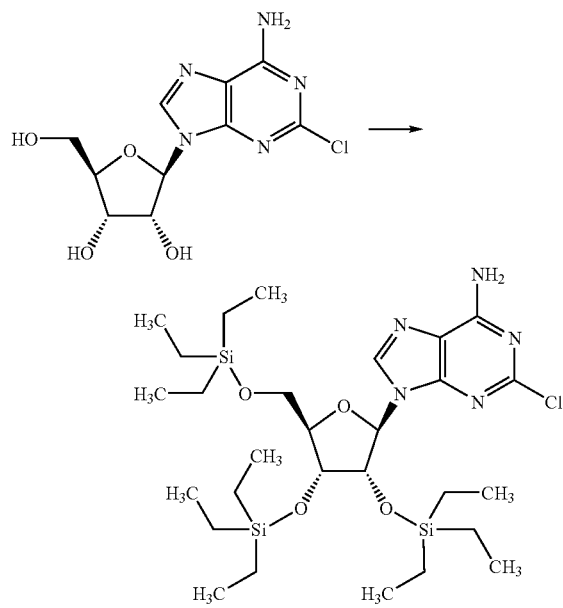

To a stirred solution of 2-chloroadenosine (5 g, 16.6 mmol) and triethylsilyl chloride (25 g, 166 mmol) in a mixture of anhydrous THF (70 mL) and DMF (30 mL) was added, in portions, imidazole (22.6 g, 332 mmol). The reaction was stirred at room temperature for 24 hours under nitrogen, at which time the reaction was complete by TLC (silica/5% MeOH in $CH_2Cl_2$). The reaction was concentrated on a rotary evaporator, diluted with ethyl acetate (80 mL), followed by 2 M NaOH (60 mL). The layers were separated, and the organic layer washed with additional 2 M NaOH (2×60 mL). After drying over $MgSO_4$, the organic extract was filtered, concentrated to a viscous oil. After passing the oil through a plug of silica gel, the desired product was obtained as a gummy, white solid. 7.2 g (67%).

$^1$H-NMR ($CDCl_3$): δ 0.38–0.56 (m, 6H), 0.58–0.76 (m, 12H), 0.81–0.92 (m, 9H), 0.93–1.08 (m, 18H), 3.77 (dd, 1H, J=11.2, 2.8 Hz), 3.93–4.05 (m, 1H), 4.07–4.16 (m, 1H), 4.34 (t, 1H, J=4.1 Hz), 4.72 (t, 1H, J=4.5 Hz), 5.96 (d, 1H, J=4.8 Hz), 6.22 (bs, 2H), 8.16 (s, 1H). LC/MS: m/z 644 (M+H).

Example 5

2-Chloro-2',3',5'-tri-O-(isopropyldimethylsilyl)adenosine

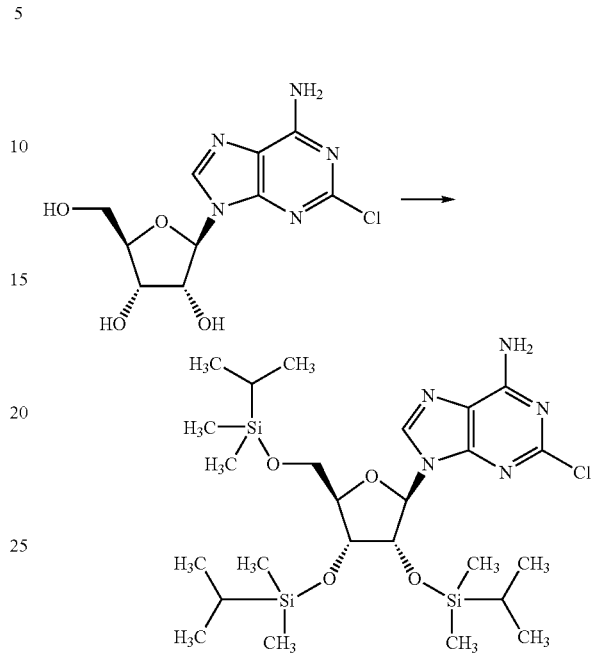

To a stirred solution of 2-chloroadenosine (5 g, 16.6 mmol) and isopropyldimethylsilyl chloride (22.7 g, 166 mmol) in a mixture of anhydrous THF (70 mL) and DMF (30 mL) was added, in portions, imidazole (22.6 g, 332 mmol). The reaction was stirred at room temperature for 18 hours under nitrogen, at which time the reaction was complete by TLC (silica/5% MeOH in $CH_2Cl_2$). The reaction was then concentrated on a rotary evaporator, diluted with ethyl acetate (80 mL), followed by 2 M NaOH (60 mL). The layers were separated, and the organic layer washed with additional 2 M NaOH (2×50 mL). After drying over $MgSO_4$, the organic extract was filtered, concentrated to afford the crude product as a white solid. After passing through a plug of silica gel, the desired product was isolated as a gummy white solid. 7.0 g (70%).

$^1$H-NMR ($CDCl_3$): δ−0.06 (s, 3H), −0.02 (s, 3H), 0.06–0.17 (m, 12H), 0.84–0.94 (m, 3H), 0.95–1.06 (m, 18H), 3.75 (dd, 1H, J=11.4, 2.8 Hz), 4.00 (dd, 1H, J=11.4, 4.2 Hz), 4.08–4.18 (m, 1H), 4.31 (t, 1H, J=4.3 Hz), 4.64 (t, 1H, J=4.4 Hz), 5.96 (d, 1H, J=4.5 Hz), 6.32 (s, 2H), 8.17 (s,1H). LC/MS: m/z 602 (M+H).

Example 6

2-Chloro-2',3',5'-tri-O-(triisopropylsilyl)adenosine

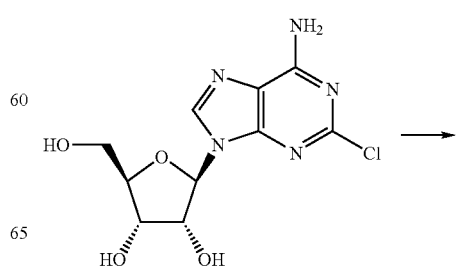

-continued

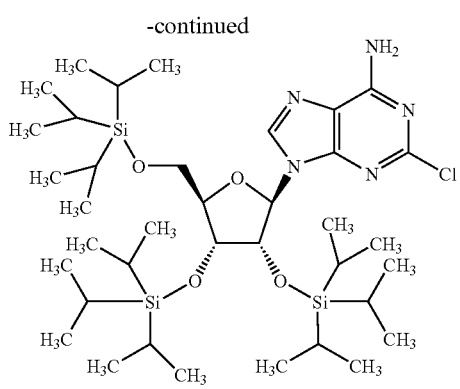

To a stirred solution of 2-chloroadenosine (5 g, 16.6 mmol) and triisopropylsilyl chloride (32 g, 166 mmol) in a mixture of anhydrous THF (65 mL) and DMF (40 mL) was added, in portions, imidazole (22.6 g, 332 mmol). The reaction was stirred at room temperature for 18 hours under nitrogen, at which time the reaction was shown to consist of three products by TLC (silica/5% MeOH in $CH_2Cl_2$). To the mixture was added 4-dimethyl-aminopyridine (50 mg) and stirring was continued an additional 48 hours. The reaction was then concentrated on a rotary evaporator, diluted with ethyl acetate (100 mL), followed by 2 M NaOH (50 mL). The layers were separated, and the organic layer washed with additional 2 M NaOH (2×50 mL). After drying over $MgSO_4$, the organic extract was filtered, concentrated to a viscous oil consisting of the desired product and two di-protected compounds. The crude product was used without further purification. LC/MS: m/z 770 (M+H); 614 (M+H for bis-protected compounds).

Example 7

2-Chloro-2',3',5'-tri-O-(isopropyldiethylsilyl)adenosine

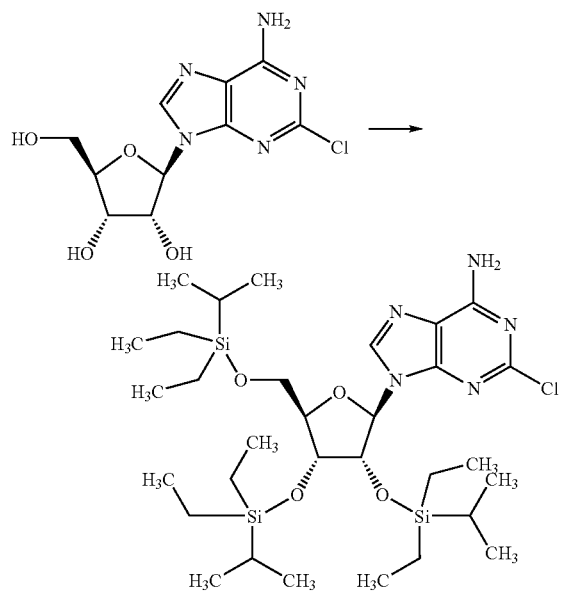

To a stirred solution of 2-chloroadenosine (5 g, 16.6 mmol) and isopropyldiethylsilyl chloride (27.4 g, 166 mmol) in a mixture of anhydrous THF (70 mL) and DMF (30 mL) was added, in portions, imidazole (22.6 g, 332 mmol). The reaction was stirred at room temperature for 18 hours under nitrogen, at which time the reaction was complete by TLC (silica/5% methanol in $CH_2Cl_2$). The reaction was then concentrated on a rotary evaporator, diluted with ethyl acetate (80 mL), followed by 2 M NaOH (60 mL). The layers were separated, and the organic layer washed with additional 2 M NaOH (3×50 mL). After drying over $MgSO_4$, the organic extract was filtered, concentrated to afford the crude product as a clear oil. The oil was passed through a plug of silica gel to afford the desired product as a clear viscous oil. 15 g (100%).

$^1$H-NMR (CDCl$_3$): δ 0.37–0.76 (m, 15H), 0.80–0.96 (m, 12H), 0.96–1.08 (m, 30H), 3.80 (dd, 1H, J=11.1, 2.9 Hz), 4.01–4.09 (m, 1H), 4.10–4.16 (m, 1H), 4.39 (t, 1H, J=3.8 Hz), 4.70–4.91 (m, 1H), 5.95 (d, 1H, J=5.2 Hz), 6.13 (br. s, 2H), 8.12 (s, 1H). LC/MS: m/z 686 (M+H).

Example 8

2-[2-(3-methylphenyl)ethoxy]-2',3',5'-tri-O-(TERT-butyldimethylsilyl)-adenosine

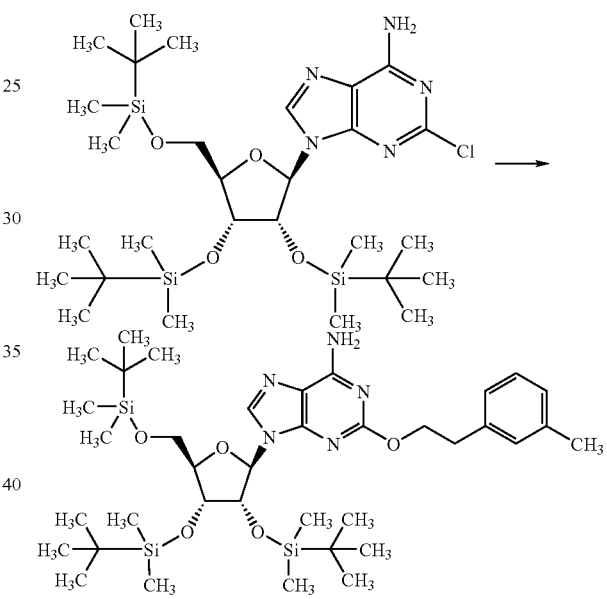

To a dry 250-mL, 3-neck roundbottom flask was added 2-chloro-2',3',5'-tri-O-(TERT-butyldimethylsilyl)adenosine (5 g, 7.8 mmol, Example 1) and 2-(3-methylphenyl)ethanol (15 mL). The mixture was flushed with nitrogen for 5–10 minutes, then heated to 50° C. To this mixture was added sodium hydride (1.56 g, 39 mmol, as a 60% dispersion in mineral oil) at such a rate as to avoid excessive gas evolution. The reaction was maintained at 50° C. until the predominant component was the product by HPLC (partially deprotected products were also seen). The reaction was then cooled to room temperature, carefully quenched with water (40 mL), and extracted with ethyl acetate (3×100 mL). The combined organic extracts were washed with brine (120 mL), dried (MgSO$_4$), filtered, and concentrated under reduced pressure to afford a brown oil. This material was purified by passing through a plug of silica gel, eluting with $CH_2Cl_2$, 5% methanol in $CH_2Cl_2$, and 10% methanol in $CH_2Cl_2$. Those fractions containing products were combined and evaporated to dryness, to afford a mixture of starting material and monosilyl-protected and disilyl-protected alkylated products in a ratio of 2:5:12. This mixture was used without further purification in the next step.

Example 9

2-[2-(3-Methylphenyl)ethoxy]adenosine

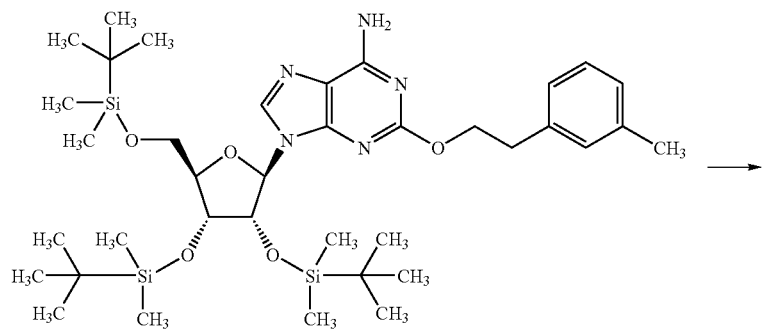

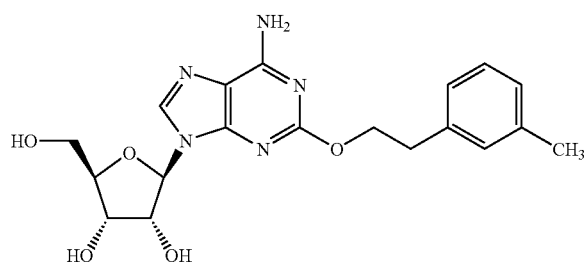

To a stirred solution of crude 2-[2-(3-methylphenyl)ethoxy]-2',3',5'-tri-O-(TERT-butyldimethylsilyl)-adenosine (5 g, Example 8) in anhydrous methanol (70 mL) under a nitrogen atmosphere was added ammonium fluoride (2.5 g, 67.5 mmol). The resulting solution was heated to reflux for 14 hours, at which time HPLC indicated the disappearance of starting material. The reaction was cooled to room temperature, concentrated in vacuo on a rotary evaporator, and the resultant solids partitioned between ethyl acetate (30 mL) and water (30 mL). The mixture was stirred for 30 minutes, the layers separated, and the aqueous portion extracted with additional ethyl acetate (2×30 mL). The combined organic layers were dried (MgSO4), filtered, and concentrated to a clear oil. The product was purified by passing the oil through a plug of silica gel, eluting with $CH_2Cl_2$, 2% methanol in $CH_2Cl_2$, 5% methanol in $CH_2Cl_2$, and 10% methanol in $CH_2Cl_2$. Fractions containing the product were combined and concentrated at reduced pressure to afford the desired product as a light yellow solid. 1.1 g (35%). m.p.: 102–108° C.

$^1$H-NMR (DMSO-$d_6$): δ 2.29 (s, 3H), 2.96 (t, 2H, J=6.9 Hz), 3.45–3.73 (m, 2H), 3.92 (q, 1H, J=3.9 Hz), 4.05–4.19 (m, 1H), 4.39 (t, 2H, J=7.0 Hz), 4.50–4.67 (m, 1H), 5.04–5.22 (m, 2H), 5.40 (d, 1H, J=6.3 Hz), 5.66–5.87 (m, 1H), 6.95–7.24 (m, 4H), 7.29 (br. s, 2H), 8.14 (s, 1H). LC/MS: m/z=402 (M+H); 95.2% purity.

Example 10

2-[2-(Cyclohexyl)ethoxy]-2',3',5'-tri-O-(TERT-butyldimethylsilyl)-adenosine

To a dry 250-mL, 3-neck roundbottom flask was added 2-chloro-2',3',5'-tri-O-(TERT-butyldimethylsilyl)adenosine (5 g, 7.8 mmol, Example 1) and 2-(cyclohexyl)ethanol (15 mL). The mixture was flushed with nitrogen for 5–10 minutes, then heated to 50° C. To this mixture was added sodium hydride (1.56 g, 39 mmol, as a 60% dispersion in mineral oil) at such a rate as to avoid excessive gas evolution. The reaction was maintained at 50° C. until the reaction was complete by HPLC. The reaction was then cooled to room temperature, carefully quenched with water (50 mL), and extracted with ethyl acetate (100 mL, 2×60 mL). The combined organic extracts were washed with brine (100 mL), dried ($MgSO_4$), filtered, and concentrated under reduced pressure to afford a viscous oil. This material was purified by passing through a plug of silica gel, eluting with $CH_2Cl_2$, 2% MeOH in $CH_2Cl_2$, 5% MeOH in $CH_2Cl_2$, and 10% MeOH in $CH_2Cl_2$. Those fractions containing products were combined and evaporated to dryness, to afford a mixture of monosilyl-protected and disilyl-protected alkylated products (LC/MS m/z=622 and 508). This mixture was used without further purification in the next step.

Example 11

2-[2-(Cyclohexyl)ethoxy]adenosine

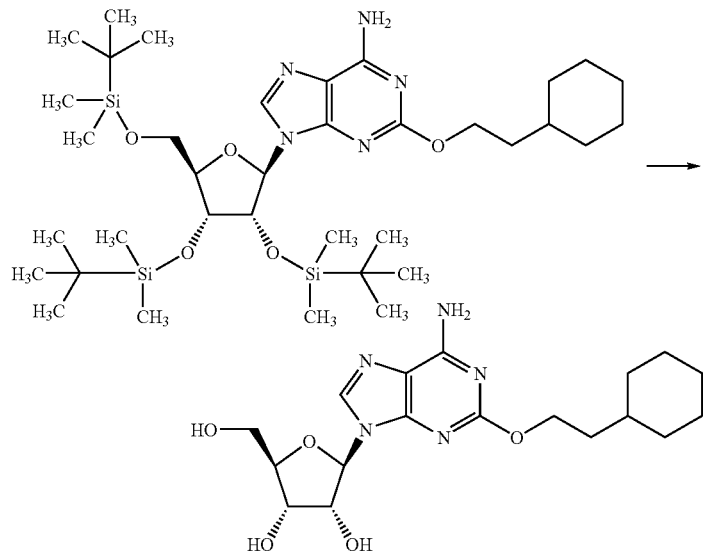

To a 100-mL one-neck round bottom flask was added under a nitrogen atmosphere 2-[2-(cyclohexyl)ethoxy]-2',3',5'-tri-O-(TERT-butyldimethylsilyl)-adenosine (3.3 g, Example 10), anhydrous methanol (50 mL), and ammonium fluoride (1.7 g, 45.8 mmol). The resulting solution was heated to reflux for 24 hours, at which time HPLC indicated the disappearance of starting material. The reaction was cooled to room temperature, concentrated in vacuo on a rotary evaporator, and the resultant solids partitioned between ethyl acetate (50 mL) and water (30 mL). The mixture was stirred for 10 minutes, the layers separated, and the aqueous portion extracted with additional ethyl acetate (50 mL). The combined organic layers were dried ($MgSO_4$), filtered, and concentrated to a light yellow solid. The product was purified by passing the oil through a plug of silica gel, eluting with $CH_2Cl_2$, 2% methanol in $CH_2Cl_2$, 5% methanol in $CH_2Cl_2$, and 10% methanol in $CH_2Cl_2$. Fractions containing the product were combined and concentrated at reduced pressure to afford the desired product as a white solid. 1.2 g (39%). m.p.: 105–112° C.

$^1$H-NMR (DMSO-$d_6$): δ 0.84–1.0 (m, 2H), 1.07–1.30 (m, 3H), 1.35–1.50 (m, 1H), 1.51–1.82 (m, 7H), 3.46–3.72 (m, 2H), 3.91 (q, 1H, J=4.0 Hz), 4.13 (bs, 1H), 4.23 (t, 2H, J=6.6 Hz), 4.59 (q, 1H, J=5.1 Hz), 5.12 (m, 2H), 5.27–5.53 (m, 1H), 5.77 (d, 1H, J=6.2 Hz), 7.25 (s, 2H), 8.13 (s, 1H). LC/MS: m/z=394 (M+H); 96.9% purity.

Example 12

2-[2-(4-Chlorophenyl)ethoxy]adenosine

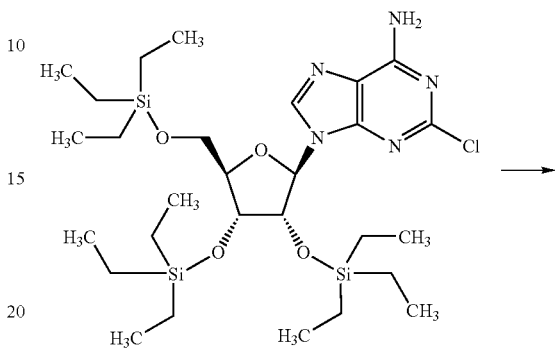

-continued

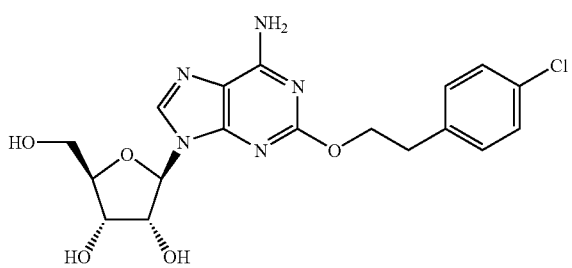

To a 250-mL, three-neck round bottom flask was added 2-chloro-2',3',5'-tri-O-(triethylsilyl)adenosine (5.0 g, 7.8 mmol, Example 4) and 2-(4-chlorophenyl)ethanol (15 mL). The mixture was flushed with nitrogen for 5–10 minutes, then heated to 50° C. To this mixture was added sodium hydride (1.56 g, 39 mmol, as a 60% dispersion in mineral oil) at such a rate as to avoid excessive gas evolution. The reaction was maintained at 50° C. for 20 hours, at which time HPLC indicated complete conversion to the fully deprotected, alkylated product. The reaction was then cooled to room temperature, carefully quenched with water (40 mL), and extracted with ethyl acetate (3×100 mL). The combined organic extracts were washed with brine (120 mL), dried (MgSO$_4$), filtered, and concentrated under reduced pressure to afford a clear oil. This material was purified by passing through a plug of silica gel, eluting with CH$_2$Cl$_2$, 3% methanol in CH$_2$Cl$_2$, and 10% methanol in CH$_2$Cl$_2$. Those fractions containing products were combined and evaporated to dryness, affording the desired product as a white solid. 680 mg (21%).m.p.: 114–120° C.

$^1$H-NMR (DMSO-d$_6$): δ 3.00 (t, 2H, J=6.7 Hz), 3.43–3.3 (m, 2H), 3.92 (q, 1H, J=3.9 Hz), 4.02–4.21 (m, 2H), 4.39 (5, 2H, J=6.7 Hz), 4.51–4.66 (m, 1H), 5.03–5.22 (m, 2H), 5.40 (d, 1H, J=6.2 Hz), 5.78 (d, 1H, J=6.1 Hz), 7.22–7.48 (m, 6H), 8.14 (s, 1H). LC/MS: m/z=422 (M+H); 95.4% purity.

Example 13

2-[2-(4-chlorophenyl)ethoxy]-2',3',5'-tri-O-(triisopropylsilyl)-adenosine

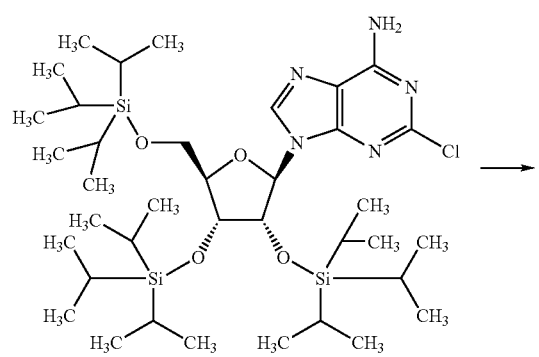

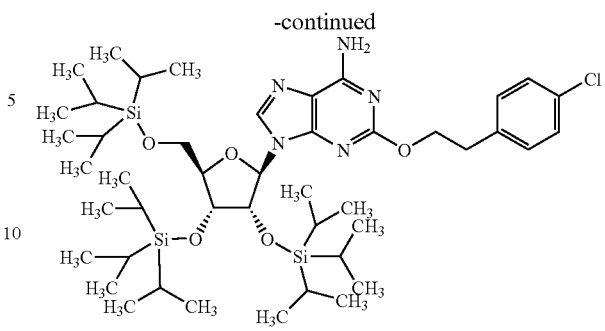

A mixture of 2-chloro-2',3',5'-tris-O-(triisopropylsilyl)adenosine (Example 6, 5.0 g) and 15 ml of 2-(4-chlorophenyl)ethyl alcohol was purged with nitrogen and heated to 50° C. Sodium hydride (1.56 g, 60% dispersion in mineral oil) was added at a rate so as to control gas evolution. After 48 hours of heating LC and LC/MS analysis showed a mixture of products with one and two protecting groups respectively (2 isomers). The reaction mixture was allowed to cool to room temperature and carefully quenched with 40 mL of water. The resulting mixture was extracted with ethyl acetate (70 ml). The layers were separated and the aqueous layer was again extracted with ethyl acetate (2×50 mL). The combined organic phases were washed with brine (80 mL), dried over MgSO$_4$ and concentrated under reduced pressure to afford a clear oil (18 g). This was purified by silica gel chromatography eluting progressively with CH$_2$Cl$_2$, 1%, 2%, 5% and then 10% MeOH in CH$_2$Cl$_2$. The fractions containing the desired products were combined and concentrated to yield 3.2 g of a gummy white solid. This mixture of silylated displacement products was taken to the next step.

Example 14

2-[2-(4-Chlorophenyl)Ethoxy]Adenosine

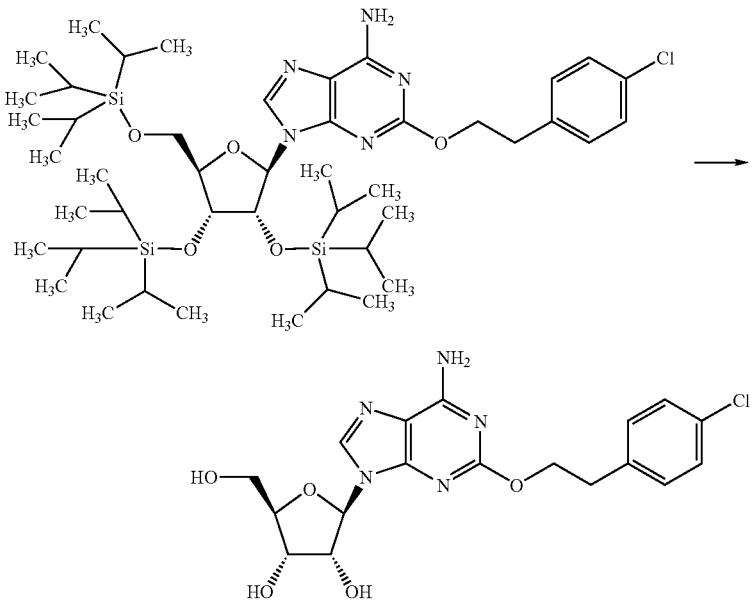

A 3.0 g portion of the crude product arising from the alkylation of 2-chloro-2',3',5'-tri-O-(triisopropylsilyl)adenosine (Example 13) was dissolved in anhydrous methanol (45 mL) under a nitrogen atmosphere and 1.4 g (37 mmol) of ammonium fluoride was added. The resulting solution was heated to reflux for 24 hours. When LC analysis showed disap-pearance of the starting material, the reaction was allowed to cool to room temperature and concentrated under reduced pressure. The residual solid was partitioned between ethyl acetate (50 mL) and water (50 mL). The aqueous layer was separated and further extracted with ethyl acetate (2×50 mL). The combined organic phases were concentrated to give 1.6 g of a white solid which was chromatographed on silica gel, eluting with $CH_2Cl_2$ and gradients of MeOH and $CH_2Cl_2$ (2–10% of MeOH). This provided 1.15 g (39% over two steps) of the desired product as a white solid. m.p. 158–161° C.

$^1$H NMR (400 MHz, DMSO-$d_6$): δ 3.00 (t, 2H, J=6.74 Hz), 3.48–3.59 (m, 1 H), 3.60–3.70 (m, 1 H), 3.91 (q, 1H, J=3.90 Hz), 4.04–4.18 (m, 2 H), 4.39 (t, 2H, J=6.69 Hz), 4.54–4.62 (m, 1 H), 5.11 (dd, 1H, J=6.30, 5.12 Hz), 5.15 (d, 1H, J=4.78 Hz), 5.39 (d, 1H, J=6.15 Hz), 5.78 (d, 1H, J=6.15 Hz), 7.30 (br. s., 2H), 7.33–7.38 (m, 4H), 8.14 (s, 1H); LC/MS: m/z=422 (M+H).

Example 15

2-[2-(-chlorophenyl)ethoxy]adenosine

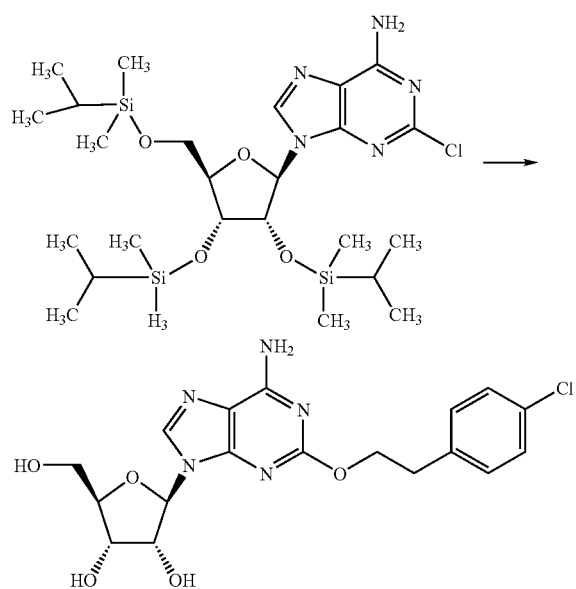

A mixture of 2-chloro-2',3',5'-tris-O-(isopropyldimethylsilyl)adenosine (Example 5, 5.0 g, 6.5 mmol) and 15 ml of 2-(4-chlorophenyl)ethyl alcohol was placed under a nitrogen atmosphere and heated to 50° C. Sodium hydride (1.30 g, 60% dispersion in mineral oil, 32.5 mmol) was added at a rate so as to control gas evolution. The reaction was then heated for 48 h at which time LC showed conversion to the fully deprotected coupling product. The reaction was allowed to cool to room temperature, carefully quenched with 40 mL of water and extracted with ethyl acetate (3×100 ml). The combined organic extracts were washed with brine (120 mL), dried over $MgSO_4$, and concentrated under reduced pressure to afford a clear oil. Chromatography on silica gel eluting with $CH_2Cl_2$, 5% MeOH in $CH_2Cl_2$, and then 10% MeOH in $CH_2Cl_2$ provided 570 mg (20.8%) of the title compound as a white solid. m.p. 158–161° C.

$^1$H NMR (400 MHz, DMSO-$d_6$): δ 3.00 (t, 2H, J=6.74 Hz), 3.48–3.59 (m, 1 H), 3.60–3.70 (m, 1 H), 3.91 (q, 1H, J=3.90 Hz), 4.04–4.18 (m, 2 H), 4.39 t, 2H, J=6.69 Hz), 4.54–4.62 (m, 1H), 5.11 (dd, 1H, J=6.30, 5.12 Hz), 5.15 (d, 1H, J=4.78 Hz), 5.39 (d, 1H, J=6.15 Hz), 5.78 (d, 1H, J=6.15 Hz), 7.30 (br. s., 2H), 7.33–7.38 (m, 4H), 8.14 (s, 1H); LC/MS: m/z=422 (M+H).

Example 16

2-[2-(4-chlorophenyl)ethoxy]-2',3',5'-tri-O-(isopropyldiethylsilyl)-adenosine

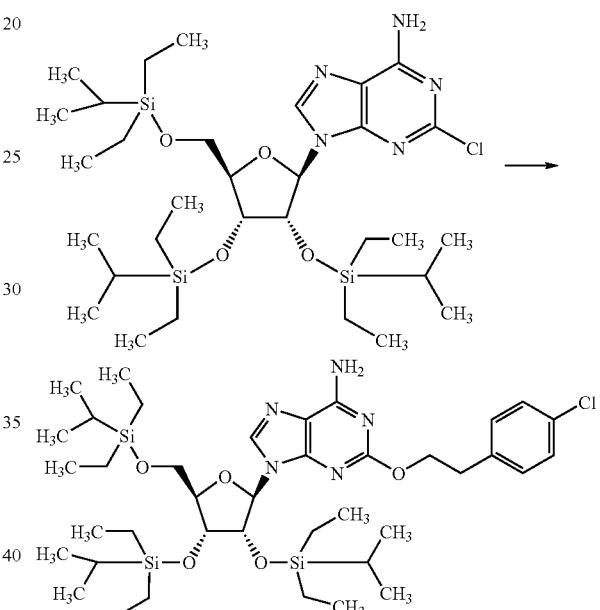

A mixture of 2-chloro-2',3',5'-tri-O-(isopropyldiethylsilyl)adenosine (Example 7, 5.0 g, 7.3 mmol) and 15 ml of 2-(4-chlorophenyl)ethyl alcohol was placed under a nitrogen atmosphere and heated to 50° C. Sodium hydride (1.6 g, 60% dispersion in mineral oil, 40 mmol) was added at such a rate as to control gas evolution. After 48 hours at 50° C., LC and LC/MS indicated the reaction mixture contained fully desilylated and partially desilylated coupling products. The reaction was then allowed to cool to room temperature, carefully quenched with 40 mL of water and partitioned with ethyl acetate (1×70 ml, 1×50 mL). The combined organic layers were washed with brine (60 mL), dried over $MgSO_4$, and concentrated under reduced pressure to furnish a clear oil. This was chromatographed on silica gel eluting progressively with $CH_2Cl_2$, and then 2%, 5% and 10% MeOH in $CH_2Cl_2$. The fractions containing the coupling products were combined and concentrated to yield 3.4 g of a gummy white solid. Analysis by LC/MS showed a mixture of the fully deprotected compound 2-[2-(4-chlorophenyl)ethoxy]adenosine (major) and a mixture products bearing one and two isopropyldiethylsilyl-protecting groups. The mixture was taken to next step without further purification.

Example 17

2-[2-(4-Chlorophenyl)ethoxy]adenosine

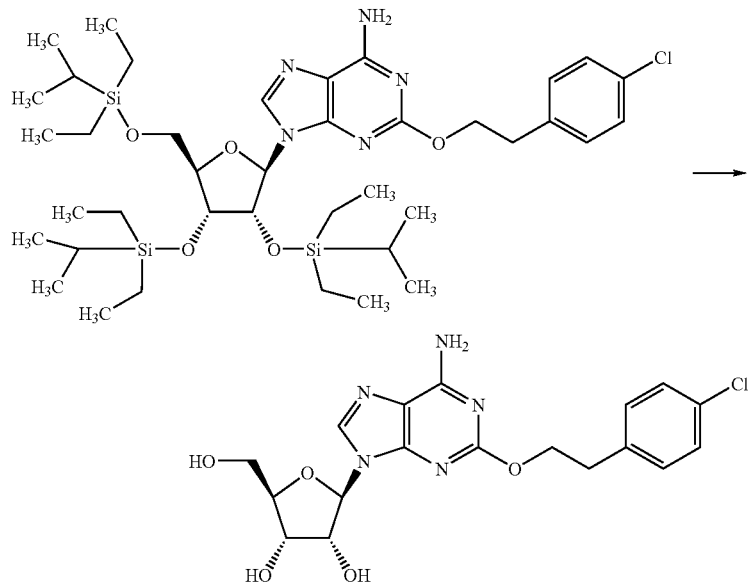

An aliquot of the mixture of 2-[2-(4-chlorophenyl)ethoxy]adenosine and partially deprotected 2-[2-(4-chlorophenyl)ethoxy]-2',3',5'-tri-O-(isopropyldiethylsilyl)adenosine (Example 16, 3.0 g) was dissolved in anhydrous methanol (42 mL) and placed under a nitrogen atmosphere. Ammonium fluoride (1.4 g, 37.2 mmol) was added and the solution was heated to reflux for 24 hours. Upon the disappearance of the starting partially deprotected intermediates, as indicated by LC analysis, the reaction was allowed to cool to room temperature and concentrated under reduced pressure. The residual solid was partitioned between 50 mL of ethyl acetate and 30 mL of water and the aqueous layer was further extracted with ethyl acetate (2×50 mL). The combined organic layers were concentrated to give 1.7 g of a white solid. Chromatography on silica gel eluting with $CH_2Cl_2$ and gradients of methanol and $CH_2Cl_2$ (2–10% of MeOH) provided 1.2 g (39%, two steps) of the desired compound as a white solid. m.p. 158–160° C.

$^1$H NMR (400 MHz, DMSO-$d_6$): δ 2.97 (t, J=6.74 Hz, 2 H) 3.45–3.56 (m, 1 H) 3.57–3.67 (m, 1 H) 3.89 (q, J=3.87 Hz, 1H) 4.00–4.17 (m, 2H) 4.37 (t J=6.74 Hz, 2H) 4.50–4.63 (m, 1H) 5.03–5.16 (m, 2 H) 5.37 (d, J=6.25 Hz, 1H) 5.75 (d, J=6.05 Hz, 1H) 7.30 (br. s., 2H) 7.31–7.36 (m, 4H) 8.12 (s, 1H); LC m/z=422 (M+H).

Example 18

2-chloro-3',5'-O-(1,1,3,3-tetraisopropyldisiloxan-1,3-diyl)adenosine

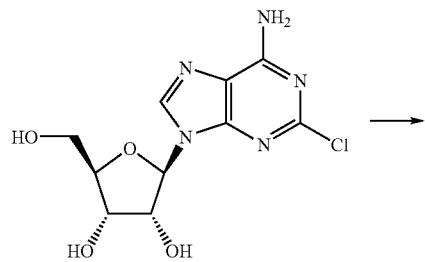

-continued

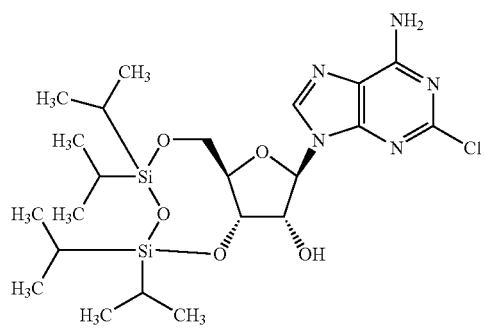

To a solution of 2-chloroadenosine (5.0 g, 17 mmol) and 1,3-dichloro-1,1,3,3-tetraisopro-pyldisiloxane (6.3 g, 20 mmol) in a mixture of 40 mL of anhydrous THF and 20 mL of DMF was added imidazole (7.91 g, 116 mmol) in portions. The solution was stirred at room temperature for 24 hours under nitrogen and then concentrated under reduced pressure. The residue was taken up in 100 mL of ethyl acetate and partitioned against 60 mL of water. The layers were separated and the organic portion was washed with 2M aqueous NaOH (2×60 mL). The organic layer was dried over $MgSO_4$ and concentrated to yield 15 g of a viscous oil The product was purified by chromatography on silica gel eluting with a gradient of 0–100% ethyl acetate in heptane to afford the desired compound as a white solid. Yield: 6.5 g (72%).

$^1$H NMR (CDCl$_3$): δ 0.91–1.17 (m, 28H) 3.37 (br s., 1H) 3.89–4.19 (m, 3H) 4.59 (dd, J=5.42, 0.93 Hz, 1H) 5.04 (dd, J=7.18, 5.61 Hz, 1H) 5.91 (d, J=1.17 Hz, 1H) 6.14 (br s., 2H) 7.91 (s, 1H); LC/MS (m/z)=544 (M+H).

Example 19

2-Chloro-3',5'-O-(1,1,3,3-tetraisopropyldisiloxan-1,3-diyl)-2'-O-triethylsilyl-adenosine

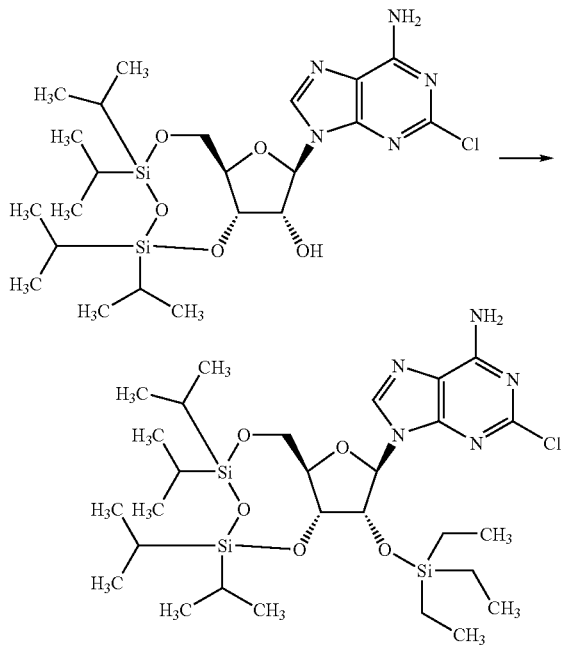

To a stirred solution of 2-chloro-3',5'-O-(1,1,3,3-tetraisopropyldisiloxan-1,3-diyl)aden-osine (Example 18, 4.0 g, 7.4 mmol) and (1.7 g, 11 mmol) of triethylsilyl chloride in a mixture of 30 mL of anhydrous THF and 15 mL of DMF under nitrogen was added imidazole (1.51 g, 22.2 mmol) in portions. The solution was stirred at room temperature for 24 hours and then additional triethylsilyl chloride (1.67 g) and imidazole (0.75 g) were added. After stirring overnight the reaction was found to be complete by TLC analysis (5% methanol in $CH_2Cl_2$) and was then concentrated by rotary evaporation. The residue was dissolved in 70 mL of ethyl acetate and washed with 2M NaOH (2×50 mL). The organic layer was dried over $Na_2SO_4$, filtered, and concentrated to yield 5.5 g of a gummy white solid. Based on TLC and LC/MS data, the isolated product was found to be a mixture of the desired product and the starting material, formed during workup. The crude product was used without further purification.

Example 20

2-[2-(4-Chlorophenyl)ethoxy]-3',5'-O-(1,1,3,3-tetraisopropyldisiloxan-1,3-diyl)-2'-O-triethylsilyl-adenosine

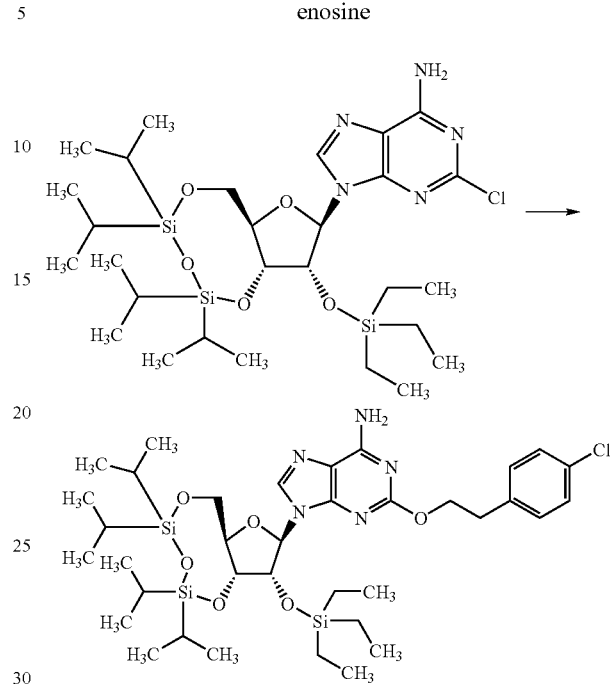

A mixture of 2-chloro-3',5'-O-(1,1,3,3-tetraisopropyldisiloxan-1,3-diyl)-2'-O-triethyl-silyl)adenosine (Example 19, 4.0 g, 6.0 mmol) and 15 ml of 2-(4-chlorophenyl)ethyl alcohol was heated to 50° C. under a nitrogen atmosphere. Sodium hydride (1.2 g, 60% dispersion in mineral oil, 30 mmol) was added at such a rate to control gas evolution. After 2 days at 50° C., the solution was cooled to room temperature and carefully quenched with water (100 mL). The mixture was extracted with ethyl acetate (3×200 ml) and the combined organic layers were washed with 300 mL of brine, dried over $MgSO_4$, and concentrated under reduced pressure. The residual brown oil was chromatographed on silica gel eluting with $CH_2Cl_2$ and then progressively with 2% to 10% methanol in $CH_2Cl_2$. Fractions containing product were combined and concentrated to yield 3.0 g of a gummy off-white solid. Analysis by LC/MS showed a mixture of the desired product and partially deprotected coupling products. This mixture was taken to next step without further purification.

Example 21

2-[2-(4-chlorophenyl)ethoxy]adenosine

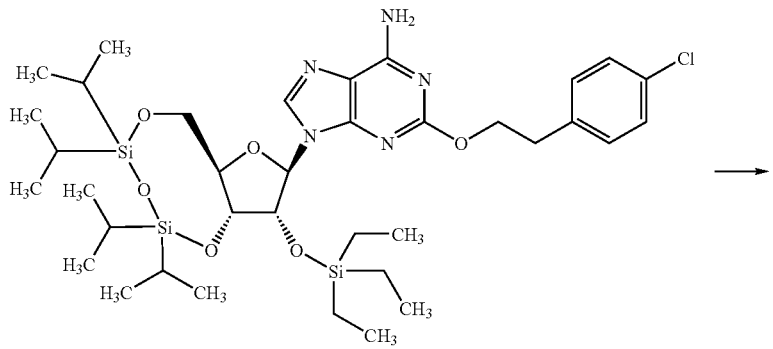

-continued

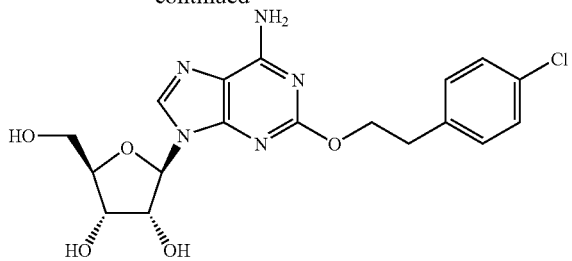

To a solution of crude 2-[2-(4-chlorophenyl)ethoxy]-3',5'-O-(1,1,3,3-tetraisopropyl-disiloxan-1,3-diyl-2'-O-triethylsilyl-adenosine (Example 21, 3.0 g) in 45 mL of anhydrous methanol was added ammonium fluoride (1.7 g, 46 mmol) and the solution was heated to reflux for 24 hours under nitrogen. Upon disappearance of the starting material as determined by LC, the reaction mixture was cooled to room temperature and concentrated under reduced pressure. The resulting solid was partitioned between 60 mL of ethyl acetate and 40 mL of water. The aqueous layer was extracted with additional ethyl acetate (2×50 mL). The combined organic phases were concentrated to give 1.7 g of a white solid that was purified on silica gel eluting with a gradient of $CH_2Cl_2$ to 10% methanol in $CH_2Cl_2$. The fractions containing the product were combined and concentrated under reduced pressure to yield 0.8 g (32%, two steps) of the desired product as a white solid. m.p. 156–159° C.

$^1$H-NMR (DMSO-d$_6$): δ 3.00 (t, 2H, J=6.74 Hz) 3.48–3.58 (m, 1H) 3.59–3.71 (m, 1H) 3.91 (q, 1H, J=3.90 Hz) 4.09–4.18 (m, 1H) 4.39 (t, 2H, J=6.74 Hz) 4.54–4.63 (m, 1H) 5.07–5.19 (m, 2H) 5.39 (d, 1H, J=6.15 Hz) 5.77 (d, 1H, J=6.05 Hz) 7.30 (br s., 2H) 7.32–7.39 (m, 4H) 8.14 (s, 1H); LC/MS: m/z=422 (M+H).

Example 22

2-Chloro -2'-O-TERT-butyldimethylsilyl-3',5'-O-(1,1,3,3-tetraisopropyldisiloxan-1,3-diyl)adenosine

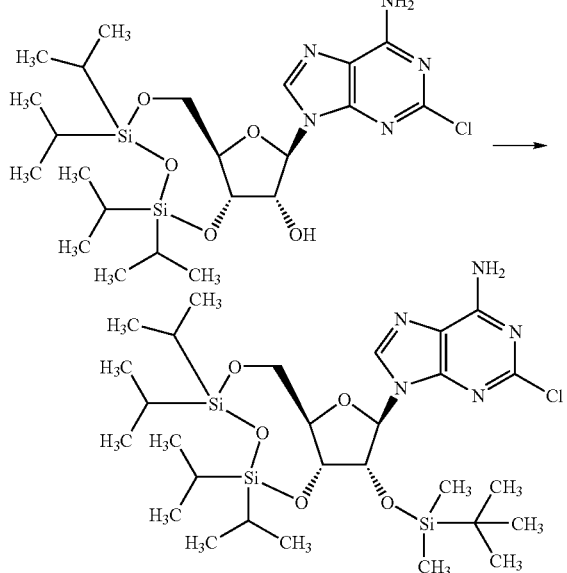

To a stirred solution of 2-chloro-(3'5'-tetraisopropyldisiloxyl)adenosine (4.0 g, 7.4 mmol) and TERT-butyldimethylsilyl chloride (1.7 g, 11.1 mmol) dissolved in a mixture of anhydrous THF (30 mL) and DMF (15 mL) was added imidazole (1.51 g, 22.2 mmol) portionwise. The reaction was stirred at room temperature for 24 hours under nitrogen, then additional TERT-butyldimethylsilyl chloride (0.9 g) and imidazole (0.75 g) were added and stirring continued. After stirring overnight, the reaction was complete based on TLC (5% methanol in $CH_2Cl_2$). The reaction mixture was concentrated by rotary evaporation, the residue was dissolved in 70 mL of ethyl acetate and partitioned with 2M NaOH (2×50 mL), dried over $Na_2SO_4$, and concentrated to yield 5.8 g of a gummy white solid.

$^1$H NMR (CDCl$_3$): δ 0.04–0.08 (s, 3H) 0.14–0.19 (s, 3H) 0.79–1.05 (m, 37H) 3.92 (dd, 1H, J=13.47, 2.44 Hz) 4.08–4.15 (m, 1H) 4.18 (d, 1H, J=13.47 Hz) 4.24–4.32 (m, 2H) 5.77 (s, 1H) 6.11 (br s, 2H) 8.09 (s, 1H); LC/MS (m/z)=658 (M+H).

Example 23

2-[2-(4-Chlorophenyl)ethoxy]-2'-O-TERT-butyldimethylsilyl-3',5'-O-(1,1,3,3-tetraisopropyldisiloxan-1,3-diyl)adenosine

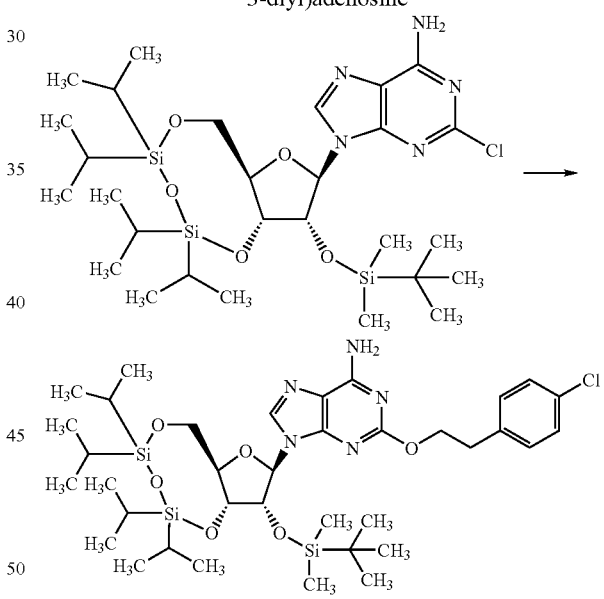

A mixture of 2-chloro-2'-O-TERT-butyldimethylsilyl-3',5'-O-(1,1,3,3-tetraisopropyl-disiloxan-1,3-diyl)adenosine (Example 22, 4.0 g, 6.0 mmol) and 2-(4-chlorophenyl)ethyl alcohol (15 mL) was heated to 50° C. and sodium hydride (1.2 g, 60% dispersion in mineral oil, 30 mmol) was added at a rate as to control gas evolution. After 2 days at 50° C., the solution was cooled to room temperature, carefully quenched with 80 mL of water and partitioned with ethyl acetate (2×100 ml). The combined organic layers were washed with 80 mL of water, 80 mL of brine, dried over MgSO$_4$, and concentrated under reduced pressure to afford 23 g of a clear oil. This was purified by chromatography on silica gel eluting with $CH_2Cl_2$ and then 1% to 10% MeOH in $CH_2Cl_2$ to provide 4.5 g of a white solid. The LC/MS showed a mixture of the desired product and partially deprotected coupling products, which was taken to next step without further purification.

Example 24

2-[2-(4-Chlorophenyl)ethoxy]adenosine

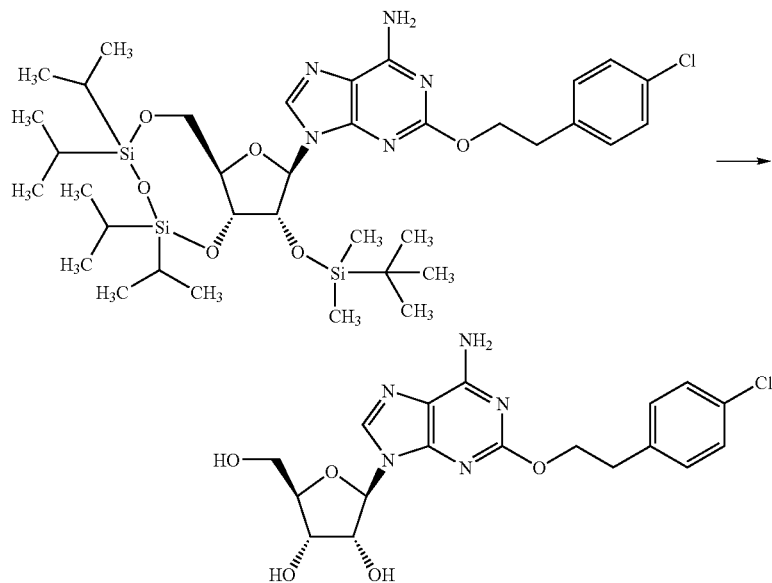

To a solution of 2-[2-(4-chlorophenyl)ethoxy]-2'-O-TERT-butyldimethylsilyl-3',5'-O (1,1,3,3-tetraisopropyldisiloxan-1,3, -diyl)adenosine (Example 23, 4.0 g) in 56 mL of anhydrous methanol was added 1.9 g (50 mmol, ~10 eq) of ammonium fluoride and the solution was heated to reflux for 18 hours under nitrogen. Upon disappearance of the starting material by as indicated by LC analysis, the reaction was cooled to room temperature and concentrated under reduced pressure. The residue was partitioned between 50 mL of water and ethyl acetate (2×60 mL). The combined organic layers were concentrated to give 3.0 g of a white solid. Chromatography on silica gel eluting with a gradient of $CH_2Cl_2$ to 10% methanol in $CH_2Cl_2$ provided 1.2 g (48%, two steps) of the desired compound as a white solid. m.p. 159–161° C.

$^1$H-NMR (DMSO-$d_6$): δ 3.00 (t, 2H, J=6.69 Hz), 3.48–3.58 (m, 1H), 3.59–3.70 (m, 1H), 3.91 (q, 1H, J=3.94 Hz), 4.09–4.19 (m, 1H), 4.39 (t, 2H, J=6.74 Hz), 4.53–4.64 (m, 1H), 5.07–5.18 (m, 2H), 5.39 (d, 1H, J=6.25 Hz), 5.77 (d, 1H, J=6.05 Hz), 7.30 (br s, 2H), 7.33–7.38 (m, 4H), 8.14 (s, 1H); LC/MS: m/z=422 (M+H).

Example 25

2-[2-(4-Methoxyphenyl)propyloxy]-2',3',5'-tri-O-(TERT-butyldimethylsilyl)adenosine

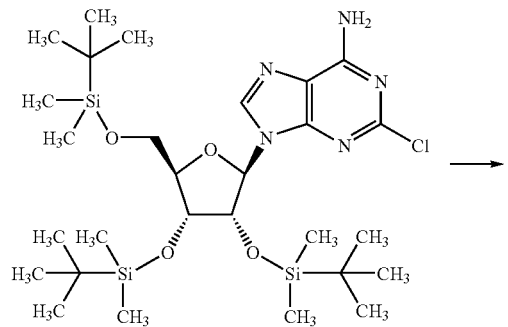

-continued

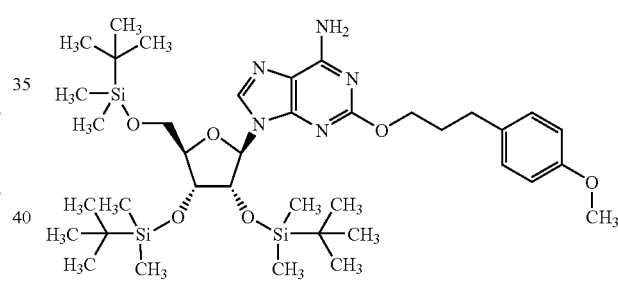

A mixture of 2-chloro-2',3',5'-tri-O-(TERT-butyldimethylsilyl)adenosine (Example 1, 5.0 g, 7.8 mmol) 3-(4-methoxyphenyl)propanol (15 mL) was placed in a round bottom flask under a nitrogen atmosphere and heated to 50° C. Sodium hydride (1.56 g, 60% dispersion in mineral oil, 39 mmol) was added at a rate so as to control gas evolution over 40 min. When LC monitoring indicated that the reaction was complete, it was carefully quenched with 50 mL of water and extracted with EtOAc (1×80 ml, 2×60 mL). The combined organic layers were washed with 100 mL of brine, dried over $MgSO_4$ and concentrated to yield 20 g of a brown oil. Chromatography on silica gel eluting progressively with $CH_2Cl_2$, and then 2%, 5% and 10% MeOH in $CH_2Cl_2$ provided 5.5 g of the desired compound as a viscous red liquid. LC/MS revealed that the product was mainly di and tri-protected product [m/z=660(M+H), 774(M+H)]. $^1$H NMR showed the presence of residual 3-(4-methoxyphenyl)propanol. The product mixture was taken to the next step without further purification.

Example 26

2-[2-(4-Methoxyphenyl)propyloxy)adenosine

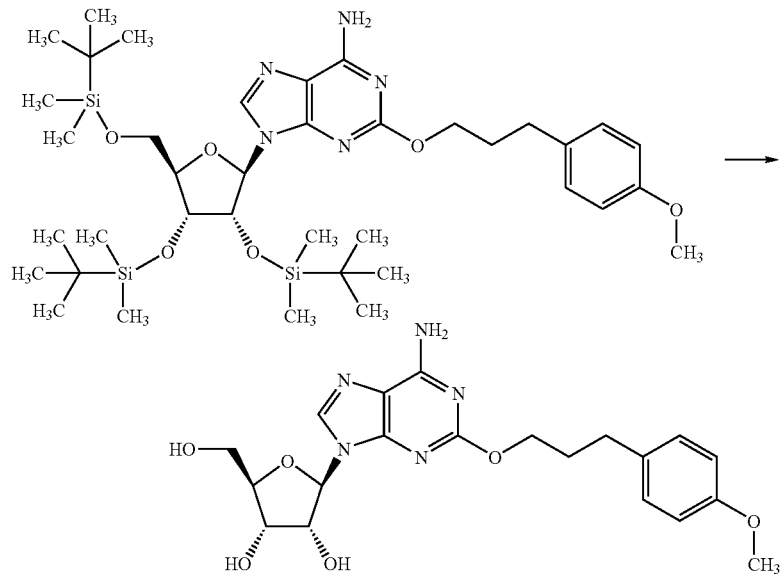

Ammonium fluoride (2.50 g, 67.5 mmol) was added to a stirred solution of 2-[2-(4-meth-oxyphenyl)propyloxy]-2',3',5'-tri-O-(TERT-butyldimethylsilyl)adenosine (Example 25, 5.0 g) in 70 mL of anhydrous MeOH. The resulting solution was heated to reflux for 24 h, cooled to room temperature, and concentrated under reduced pressure. The residual yellow solid was partitioned between 60 mL of water and ethyl acetate (2×60 mL) and the combined organic layers were concentrated to give 3 g of a yellow solid. Chromatography on silica gel eluting with a gradient of 0–10% methanol in $CH_2Cl_2$ furnished 0.9 g (27%) of the desired product as a yellow solid. m.p. 90–105° C.

$^1$H-NMR (DMSO-d$_6$): δ 1.88–2.01 (m, 2H), 2.60–2.70 (m, 2H), 3.47–3.58 (m, 1H), 3.60–3.69 (m, 1H), 3.71 (s, 3H), 3.91 (q, 1H, J=3.90 Hz), 4.06–4.16 (m, 1H), 4.18 (t, 2H, J=6.44 Hz), 4.59 (q, 1H, J=6.05 Hz), 5.12 (dd, 1H, J=6.30, 5.22 Hz), 5.15 (d, 1H, J=4.69 Hz), 5.39 (d, 1H, J=6.25 Hz), 5.77 (d, 1H, J=6.05 Hz), 6.81–6.89 (m, 2H), 7.09–7.18 (m, 2H), 7.27 (br s, 2H), 8.14 (s, 1H); LC/MS: m/z=432 (M+H).

Example 27

2-[2-(thiophen-2-yl)ethoxy]-2',3',5'-tri-O-(TERT-butyldimethylsilyl)-adenosine

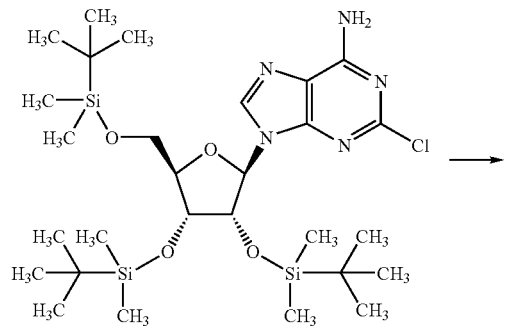

-continued

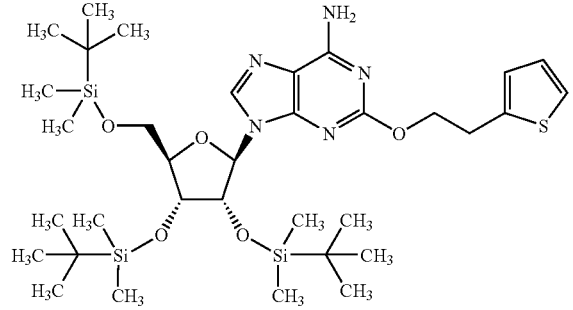

A mixture of 2-chloro-2',3',5'-tri-O-(tert-butyldimethylsilyl)adenosine) (Example 1, 1.0 g, 1.5 mmol) and 2-(thiophen-2-yl)ethyl alcohol (5 mL) was heated to 50° C. in a roundbottom flask under a nitrogen atmosphere. Sodium hydride (300 mg, 60% dispersion in mineral oil, 7.7 mmol) was added at a rate so as to control gas evolution. Once complete, the reaction was allowed to cool to room temperature and was carefully quenched with 10 mL of water, then extracted with ethyl acetate (3×20 ml). The combined organic phases were washed with 50 mL of brine, dried over $MgSO_4$, and concentrated to give a brown oil that was purified by chromatography on silica gel eluting with a gradient of 0–10% methanol in $CH_2Cl_2$. This afforded 361 mg (33%) of 2-[2-(thiophen-2-yl)ethoxy]-2',3',5'-tri-O-(TERT-butyldimethylsilyl)adenosine as an off-white solid which was used without further purification

Example 28

2-[2-(thiophen-2-yl)ethoxy]adenosine

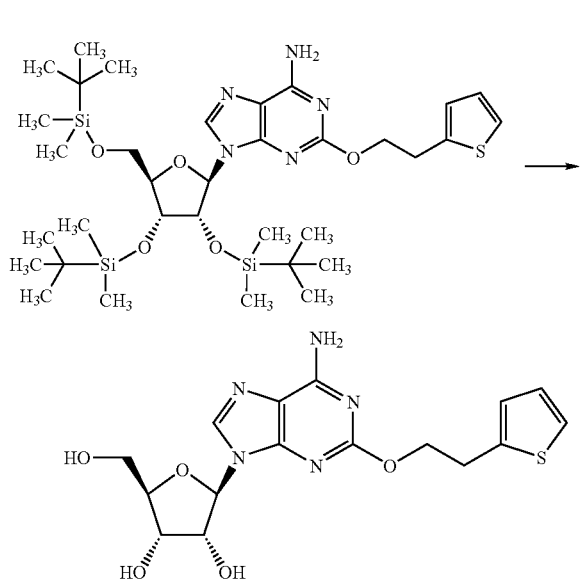

A solution of 361 mg of 2-[2-(thiophen-2-yl)ethoxy]-2',3',5'-tri-O-(TERT-butyldimethylsilyl)adenosine (Example 27, 0.361 g) in 7 mL of methanol was flushed with nitrogen. To this solution was added ammonium fluoride (100 mg) and the mixture was heated to 60° C. overnight. Once the disappearance of starting material was complete by TLC analysis, the reaction was concentrated to dryness. To the residue was added 10 mL, of water and 20 mL of ethyl acetate and the biphasic mixture was stirred for 10 min. The layers were separated, the organic extract collected, and the aqueous layer extracted two more times with ethyl acetate. The combined organic layers were concentrated to dryness and the crude product purified using over silica, eluting with a gradient of 0–10% methanol in $CH_2Cl_2$ to obtain the desired compound as a white solid. Yield: 106 mg (55%). m.p. 112–130° C.

$^1$H NMR (DMSO-$d_6$): δ 3.20 (t, 2H, J=6.54 Hz), 3.44–3.68 (m, 2H), 3.89 (q, 1H, J=3.90 Hz), 4.02–4.15 (m, 1H), 4.39 (t, 2H, J=6.59 Hz), 4.56 (q, 1H, J=6.02 Hz), 5.01–5.10 (m, 1H), 5.13 (d, 1H, J=4.78 Hz), 5.38 (d, 1H, J=6.15 Hz), 5.75 (d, 1H, J=6.15 Hz), 6.90–6.98 (m, 2H), 7.19–7.39 (m, 3H), 8.12 (s, 1H); LC/MS: m/z=394 (M+H).

Example 29

2-[2-(4-Chlorophenyl)ethoxy]adenosine

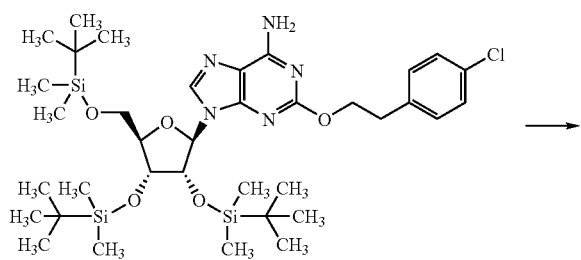

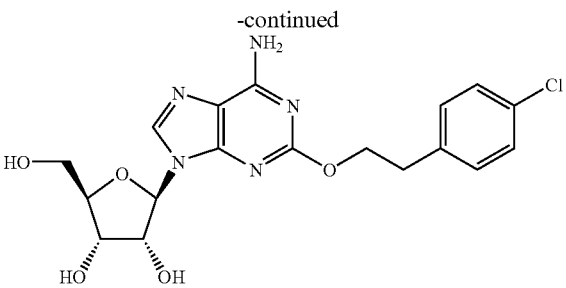

To a solution of 2-[2-(4-chlorophenyl)ethoxy]-2',3',5'-tri-O-(TERT-butyldimethylsilyl)-adenosine (Example 1, 500 mg, 0.654 mmol) in 7 mL of anhydrous methanol flushed with nitrogen was added 532 μL (3.3 mmol, 5 eq.) of triethylamine trihydrofluoride. The reaction was heated to 50° C. for 18 hours. On disappearance of the starting material as indicated by LC analysis, the reaction was allowed to cool which resulted in precipitation of a white solid. This was collected by filtration, rinsed with 3 mL of methanol and dried to provide 171 mg (62%) of the desired product as a white solid.

$^1$H-NMR (DMSO-$d_6$): δ 3.00 (t, 2H, J=6.7 Hz), 3.48–3.58 (m, 1H), 3.59–3.71 (m, 1H), 3.91 (q, 1H, J=3.9 Hz), 4.09–4.18 (m, 1H), 4.39 (t, 2H, J=6.7 Hz), 4.54–4.63 (m, 1H), 5.07–5.19 (m, 2H), 5.39 (d, 1H, J=6.1 Hz), 5.77 (d, 1H, J=6.1 Hz), 7.30 (br s, 2H), 7.32–7.39 (m, 4H), 8.14 (s, 1H); LC/MS: m/z=422 (M+H).

Example 30

2-[2-(4-Chlorophenyl)ethoxy]adenosine

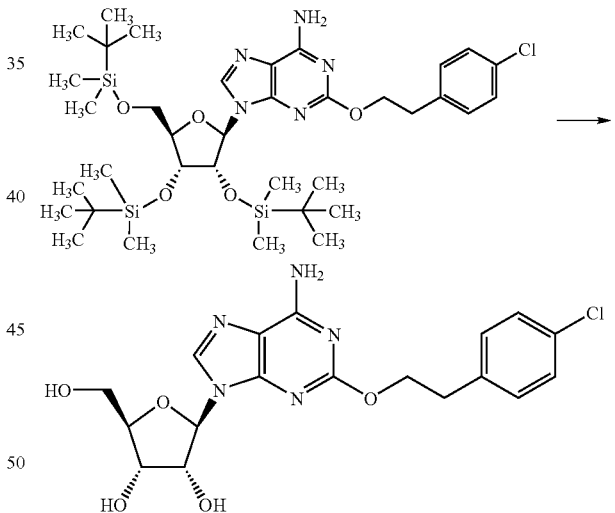

To a solution of 2-[2-(4-chlorophenyl)ethoxy]-2',3',5'-tri-O-(TERT-butyldimethylsilyl)-adenosine (Example 1, 500 mg, 0.654 mmol) in 7 mL of anhydrous methanol flushed with nitrogen was added 323 mg (5 equiv.) of hydrogen fluoride-pyridine. The reaction was heated to 50° C. for 18 hours. Upon disappearance of the starting material as indicated by LC analysis, the reaction was allowed to cool to room temperature, which resulted in precipitation of a white solid. This was collected by filtration, rinsed with 3 mL of methanol and dried to obtain 138 mg (50%) of the desired product as a white solid.

$^1$H-NMR (DMSO-$d_6$): δ 3.00 (t, 2H, J=6.74 Hz), 3.48–3.58 (m, 1H), 3.59–3.71 (m, 1H), 3.91 (q, 1H, J=3.90 Hz), 4.09–4.18 (m, 1H), 4.39 (t, 2H, J=6.74 Hz), 4.54–4.63 (m, 1H), 5.07–5.19 (m, 2H), 5.39 (d, 1H, J=6.15 Hz), 5.77

(d, 1H, J=6.05 Hz), 7.30 (br s, 2H), 7.32–7.39 (m, 4H), 8.14 (s, 1H); LC/MS: m/z=422 (M+H).

Example 31

2-[2-(4-Chlorophenyl)ethoxy]adenosine

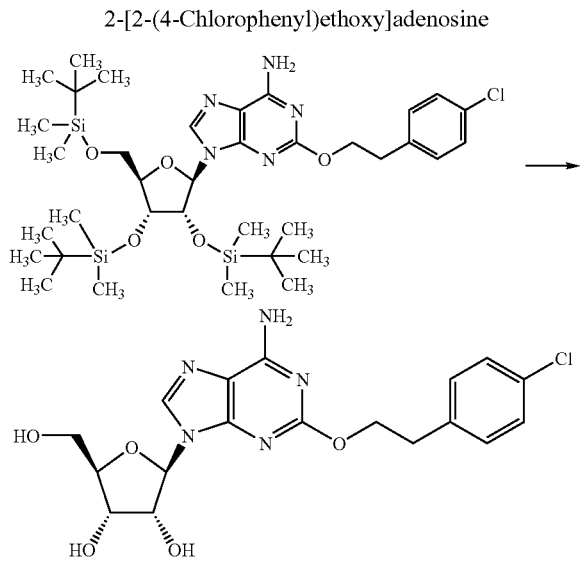

To a solution of 2-[2-(4-chlorophenyl)ethoxy]-2',3',5'-tri-O-(TERT-butyldimethylsilyl)-adenosine (Example 1, 500 mg, 0.654 mmol) in 7 mL of anhydrous methanol flushed with nitrogen was added 3.27 mL of a 1.0 M solution of TBAF in THF (5 equiv). The reaction was heated to 50° C. for 48 hours. Upon disappearance of the starting material as indicated by LC/MS analysis, the reaction mixture was allowed to cool to room temperature and was concentrated to dryness. Ethyl acetate (20 ml) and water (20 ml) were added and stirred for 5 minutes. The layers were separated and the aqueous layer reextracted with ethyl acetate (2×20 ml). The organic phases were combined, dried over MgSO$_4$ and concentrated to give an oil. The crude material was then purified on silica gel, eluting with a gradient of 0%-10% methanol in CH$_2$Cl$_2$, affording 128 mg (46%) of the desired product as a white solid.

$^1$H-NMR (DMSO-d$_6$): δ 3.00 (t, 2H, J=6.74 Hz) 3.48–3.58 (m, 1H) 3.59–3.71 (m, 1H) 3.91 (q, 1H, J=3.90 Hz) 4.09–4.18 (m, 1H) 4.39 (t, 2H, J=6.74 Hz) 4.54–4.63 (m, 1H) 5.07–5.19 (m, 2H) 5.39 (d, 1H, J=6.15 Hz) 5.77 (d, 1H, J=6.05 Hz) 7.30 (br s., 2H) 7.32–7.39 (m, 4H) 8.14 (s, 1H); LC/MS: m/z=422 (M+H).

These examples are preferred embodiments only, and are provided to illustrate this invention. They are not intended, either individually, in combination, or collectively, to define the full scope of the invention.

We claim:

1. A method for the preparation of a compound of the formula

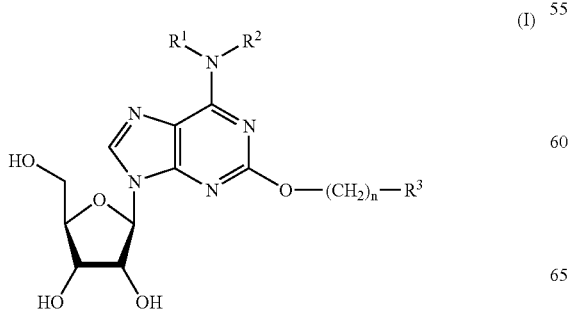

(I)

wherein

R$^1$ and R$^2$ are independently selected from hydrogen, C$_1$–C$_6$ alkyl, C$_2$–C$_6$ alkenyl, C$_2$–C$_6$ alkynyl, C$_3$–C$_8$ cycloalkyl, C$_3$–C$_8$ cycloalkenyl, C$_7$–C$_{12}$ aralkyl, C$_6$–C$_{12}$ aryl, 5–7 membered heteroaryl, and 4–7 membered heterocycloalkyl, each of which is optionally substituted with 1 to 3 substituents independently selected from the group consisting of C$_1$–C$_6$ alkyl, C$_1$–C$_6$ alkoxy, amino, mono-(C$_1$–C$_6$ alkyl)amino, di-(C$_1$–C$_6$ alkyl)amino, halogen, hydroxy, cyano, nitro, carboxylate, carboxamide, sulfonate, and sulfonamide; or NR$^1$R$^2$ taken in combination forms a 4–7 membered heterocycloalkyl or a 5–7 membered heteroaryl group, each of which is optionally substituted with 1 to 3 substituents independently selected from the group consisting of C$_1$–C$_6$ alkyl, C$_1$–C$_6$ alkoxy, amino, mono-(C$_1$–C$_6$ alkyl)amino, di-(C$_1$–C$_6$ alkyl)amino, halogen, hydroxy, cyano, nitro, carboxylate, carboxamide, sulfonate, and sulfonamide;

R$^3$ is aryl, cycloalkyl or heteroaryl, each of which is optionally substituted with 1 to 3 substituents independently selected from the group consisting of alkyl, alkoxy, and halogen; and n is an integer of 2 or 3; which method comprises:

a) protecting the hydroxyl groups of a compound of the formula

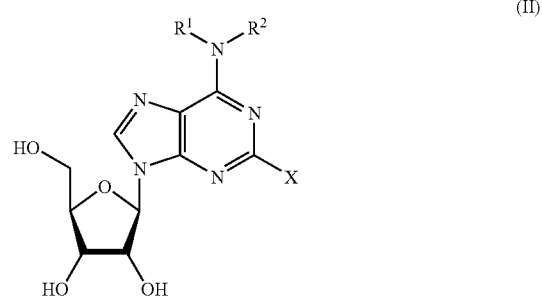

(II)

wherein R$^1$ and R$^2$ have a meaning as described for formula (I), and X represents halogen, mesylate, tosylate or triflate, to afford a compound of the formula

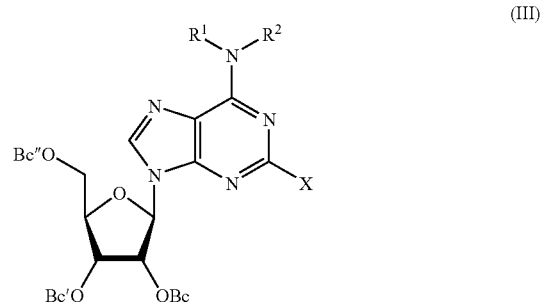

(III)

wherein R$^1$, R$^2$ and X have a meaning as described above, and Bc, Bc' and Bc" represent, independently from each other, the same or a different silyl group of the formula, —SiR$_A$R$_B$R$_C$, in which R$_A$, R$_B$, and R$_C$ are, independently from each other, C$_1$–C$_6$ alkyl, phenyl or benzyl; or Bc represents a silyl group of the formula, —SiR$_A$R$_B$R$_C$, in which R$_A$, R$_B$, and R$_C$ are, independently from each other, C$_1$–C$_6$ alkyl; and Bc' and B" combined are 1,1,3,3-tetraisopropyl-disiloxan-1,3-diyl;

treating a resulting compound of formula (III) in the absence of an extrinsic solvent with an alcohol of the formula

R$^3$(CH$_2$)$_n$OH  (IV)

wherein R$^3$ and n have a meaning as described for formula (I), and a strong base, to afford a compound of the formula

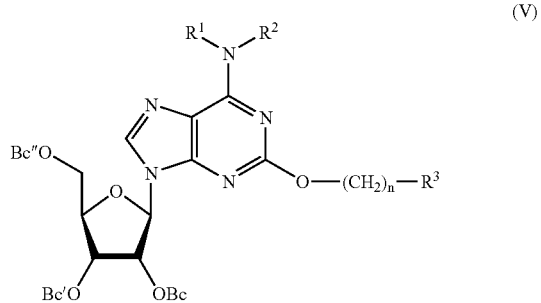

(V)

wherein R$^1$, R$^2$, R$^3$, Bc, Bc', Bc" and n have a meaning as described above; and removing the silyl groups of a resulting compound of formula (V) to afford a compound of formula (I) wherein R$^1$, R$^2$, R$^3$ and n have a meaning as described above.

2. The method of claim 1, wherein Bc, Bc' and Bc" are, independently from each other, a silyl group of the formula, —SiR$_A$R$_B$R$_C$, in which R$_A$, R$_B$, and R$_C$ are, independently from each other, C$_1$–C$_6$ alkyl.

3. The method of claim 2, wherein R$_A$ is C$_3$–C$_6$ alkyl and R$_B$ and R$_C$ are, independently from each other, C$_1$–C$_4$ alkyl.

4. The method of claim 2, wherein Bc, Bc' and Bc" are the same silyl group selected from the group consisting of t-butyldimethylsilyl, triethylsilyl, isopropyldiethylsilyl, triisopropylsilyl, isopropyldimethylsilyl and diisopropylethylsilyl.

5. The method of claim 4, wherein R$^3$ is 4-chlorophenyl and n is 2.

6. The method of claim 5, wherein the strong base in step (b) is sodium hydride.

7. The method of claim 4, wherein the removal of the silyl groups in step (c) is accomplished with a fluoride salt or a base adduct of hydrogen fluoride.

8. The method of claim 7, wherein the removal of the silyl groups in step (c) is accomplished with a fluoride salt comprising a tetra(C$_1$–C$_{10}$)alkylammonium cation.

9. The method of claim 8, wherein the fluoride salt is selected from the group consisting of tetramethylammonium fluoride, tetraethylammonium fluoride and tetrabutylammonium fluoride.

10. The method of claim 9, wherein the fluoride salt is tetrabutylammonium fluoride.

11. The method of claim 7, wherein the removal of the silyl groups in step (c) is accomplished with a base adduct of hydrogen fluoride selected from the group consisting of hydrogen fluoride-pyridine, hydrogen fluoride-pyrazine, hydrogen fluoride-pyrimidine, hydrogen fluoride-trialkylamine, hydrogen fluoride-piperidine, hydrogen fluoride-pyrrole and hydrogen fluoride-pyrrolidine.

12. The method of claim 11, wherein the base adduct of hydrogen fluoride is selected from the group consisting of triethylamine trihydrofluoride and hydrogen fluoride-pyridine.

13. The method of claim 1, wherein Bc is a silyl group of the formula, —SiR$_A$R$_B$R$_C$, in which R$_A$, R$_B$, and R$_C$ are, independently from each other, C$_1$–C$_6$ alkyl, and Bc' and B" combined are 1,1,3,3-tetraisopropyl-disiloxan-1,3-diyl.

14. The method of claim 13, wherein Bc is selected from the group consisting of t-butyldimethylsilyl, triethylsilyl, isopropyldiethylsilyl, triisopropylsilyl, isopropyldimethylsilyl and diisopropylethylsilyl.

15. The method of claim 14, wherein R$^3$ is 4-chlorophenyl and n is 2.

16. The method of claim 15, wherein the strong base in step (b) is sodium hydride.

17. The method of claim 14, wherein the removal of the silyl groups in step (c) is accomplished with a fluoride salt or a base adduct of hydrogen fluoride.

18. The method of claim 17, wherein the removal of the silyl groups in step (c) is accomplished with a fluoride salt comprising a tetra(C$_1$–C$_{10}$)alkylammonium cation.

19. The method of claim 18, wherein the fluoride salt is selected from the group consisting of tetramethylammonium fluoride, tetraethylanunonium fluoride, and tetrabutylanimonium fluoride.

20. The method of claim 19, wherein the fluoride salt is tetrabutylanimonium fluoride.

21. The method of claim 17, wherein the removal of the silyl groups in step (c) is accomplished with a base adduct of hydrogen fluoride selected from the group consisting of hydrogen fluoride-pyridine, hydrogen fluoride-pyrazine, hydrogen fluoride-pyrimidine, hydrogen fluoride-trialkylamine, hydrogen fluoride-piperidine, hydrogen fluoride-pyrrole and hydrogen fluoride-pyrrolidine.

22. The method of claim 21, wherein the base adduct of hydrogen fluoride is selected from the group consisting of triethylamine trihydrofluoride and hydrogen fluoride-pyridine.

23. The method of claim 1, wherein R$^1$ and R$^2$ are hydrogen.

24. A method of accelerating healing of a wound in a mammal which method comprises administering topically to said wound a pharmaceutical composition comprising 2-[2-(4-chlorophenyl)ethoxy]adenosine.

25. The method of claim 24, wherein the wound is a diabetic foot ulcer.

* * * * *